(12) United States Patent
Cnops et al.

(10) Patent No.: US 7,829,758 B2
(45) Date of Patent: Nov. 9, 2010

(54) MODULATION OF PLANT CELL NUMBER

(75) Inventors: Gerda Cnops, Ghent (BE); Delphine Fleury, Belair (AU); Dirk G. Inze, Moorsel-Aalst (BE); Maria van Lijsebettens, Merelbeke (BE)

(73) Assignees: VIB VZW, Zwijnaarde (BE); Universiteit Gent, Ghent (BE)

( * ) Notice: Subject to any disclaimer, the term of this patent is extended or adjusted under 35 U.S.C. 154(b) by 505 days.

(21) Appl. No.: 11/660,483

(22) PCT Filed: Aug. 16, 2005

(86) PCT No.: PCT/EP2005/054031

§ 371 (c)(1),
(2), (4) Date: Apr. 22, 2008

(87) PCT Pub. No.: WO2006/027310

PCT Pub. Date: Mar. 16, 2006

(65) Prior Publication Data

US 2008/0271208 A1  Oct. 30, 2008

(30) Foreign Application Priority Data

Aug. 18, 2004 (EP) .................... 04103971

(51) Int. Cl.
*C12N 15/82* (2006.01)
(52) U.S. Cl. ............ 800/278; 800/287; 800/290
(58) Field of Classification Search .......... None
See application file for complete search history.

(56) References Cited

U.S. PATENT DOCUMENTS

| 2002/0040490 A1 | 4/2002 | Gorlach et al. |
| 2004/0034888 A1 | 2/2004 | Liu et al. |
| 2004/0123349 A1* | 6/2004 | Xie et al. ............. 800/287 |

FOREIGN PATENT DOCUMENTS

EP  1 033 405 A2  9/2000

OTHER PUBLICATIONS

Mukoko Bopopi et al (2010, Journal of Experimental Botany 61(1):297-310).*
PCT International Search Report, PCT/EP2005/054031, dated Mar. 17, 2006.
Berna, Genoveva, et al., A Mutational Analysis of Leaf Morphogenesis in *Arabidopsis thaliana*, Genetics, Jun. 1999, pp. 729-742, vol. 152, Genetics Society of America.
Database EMBL 'Online! Mar. 25, 2002 "*Arabidopsis thaliana* unknown protein, mRNA, complete cds," retrieved from EBI accession No. EM_PRO:AY081322, Database accession No. AY081322.
Kraft, Edward, et al., Functional Analysis of the RINGtype Ubiquitin Ligase Family of Arabidopsis, Abstract Book of the 15th International Conference on Arabidopsis Research, Jul. 11-14, 2005, Berlin, Germany, 2004, Abstract #03-080, 3 pages.

* cited by examiner

*Primary Examiner*—Stuart F. Baum
(74) *Attorney, Agent, or Firm*—TraskBritt

(57) ABSTRACT

The present invention relates to the use of the ANG4 gene, or a variant thereof, to modulate the cell number of a plant organ. Said modulation can be used to increase the plant biomass, or to adapt the plant architecture.

12 Claims, 9 Drawing Sheets

Fig. 6:

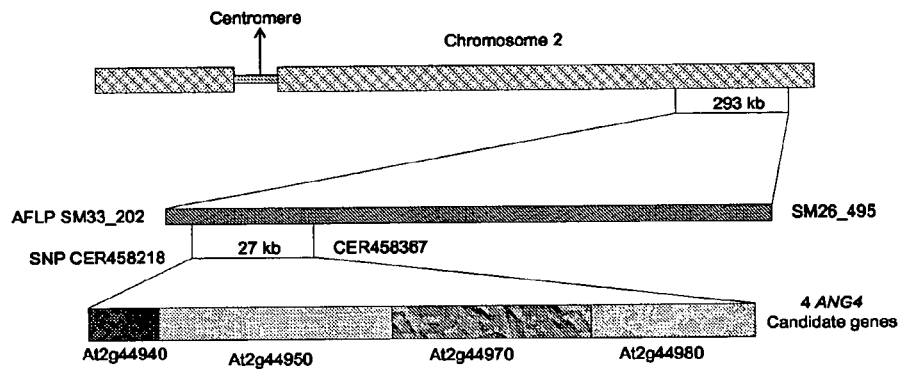

Fig. 7:

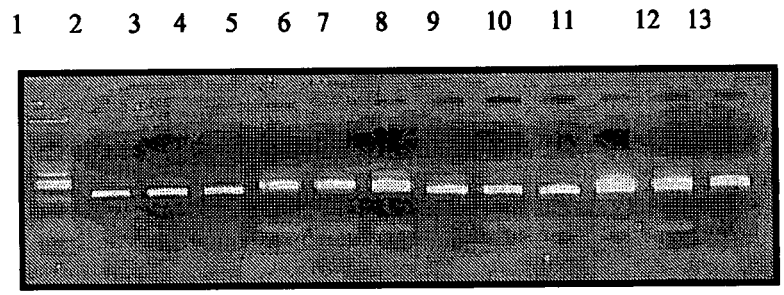

Fig. 8:

| Ang4_1 | AATCATCAAGAATTGAAGATTAGGTATATCTGTGTGTGCCCGTATGCTCAAA |
| Ang4_2 | AATCATCAAGAATTGAAGATTAGGTATATCTGTGTGTGCCCGTATGCTCAAA |
| Ang4_3 | AATCATCAAGAATTGAAGATTAGGTATATCTGTGTGTGCCCGTATGCTCAAA |
| Ler_1 | AATCATCAAGAATTGAAGATCAGGTATATCTGTGTGTGCCCGTATGCTCAAA |
| Ler_2 | AATCATCAAGAATTGAAGATCAGGTATATCTGTGTGTGCCCGTATGCTCAAA |
| Ler_3 | AATCATCAAGAATTGAAGATCAGGTATATCTGTGTGTGCCCGTATGCTCAAA |

Fig. 9:

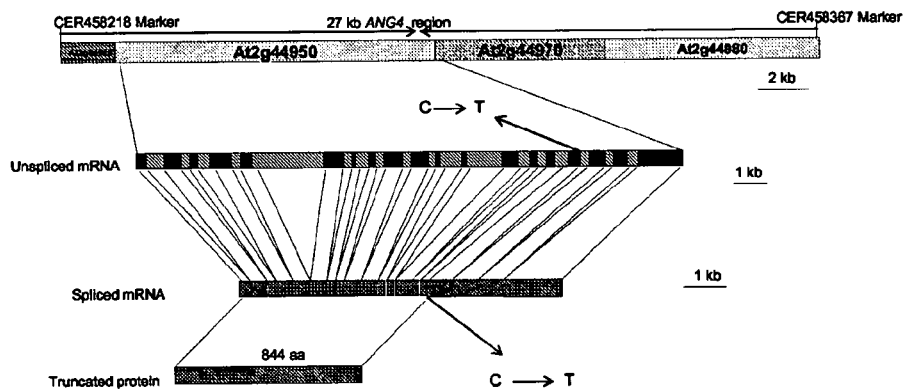

Fig. 10:

```
TAIR_At2g44950      ---MASTGEPDRKRRHFSSISPSE-AAAAVKKQ--------------PFFWPSSEDK-L
CAD41603.3          ---MGSTGEPDRKRRLSSSVAPGGGAPVSPAKR--------------LAVAPTSEDKKL
MIPS_At1g55250      MENQESDEPMQKKPHLLDSVPNSMARNSSPSHPIAKSVSFFDCDFSLLCLRLVDYEIDV
NP922769.1          ------------------------------------------------------------M
AAP36593.1          ---MSGPGNKRAAGD-GGSGPPEKKLSREEKTTTTL---------IEPIRLGGISSTEEM
NP055586_RFP_40     ---MSGPGNKRAAGD-GGSGPPEKKLSREEKTTTTL---------IEPIRLGGISSTEEM
AAK58539_RFP_20     ---MSGIGNKRAAGEPGTSMPPEKKAAVEDSGTT-----------VETIKLGGVSSTEEL

TAIR_At2g44950      DTAVLQFQNLKLSQKLEAQQVECSILEDKLSQIKEKQLPYNSSLKTVHKSWEKLTASVES
CAD41603.3          DFTVLKYKNQKLSEQLEAHKFEYRALENKFAGLKEKQRTHNETLSLVNSSWEQLVADLKS
MIPS_At1g55250      DATVLQLQNQKLVQQLDLQKKQLYDVESKIQELQLNQTSYDDELISVNQLWNQLVDDLIL
NP922769.1          DAAALQYENQKLVQQLEAQKSKMRALEGKFKELRDEQCSYDNTLICLNKMWNQLIDDLVL
AAP36593.1          DLKVLQFKNKKLAERLEQRQACEDELRERIEKLEKRQATDDATLLIVNRYWAQLDETVEA
NP055586_RFP_40     DLKVLQFKNKKLAERLEQRQACEDELRERIEKLEKRQATDDATLLIVNRYWAQLDETVEA
AAK58539_RFP_20     DIRTLQTKNRKLAEMLDQRQAIEDELREHIEKLERRQATDDASLLIVNRYWSQFDENIRI

TAIR_At2g44950      ---CSVRVSDS--------------SSGAHRFVN-KEDGSSPAVKNDFINRLLETGATES
CAD41603.3          RSFCKSGSPNS--------------SPGSGHNNV-QKDGTCAPIERDTLRSLVESGATES
MIPS_At1g55250      LGVRAGANQEA--------------LNYLDIVDK--KRVPPCAADETFLCRLLQVDSLDT
NP922769.1          LGVRAGGDLNG--------------LQALDHEEMSEESLESCPSEEIFLFRLLNSRNFRN
AAP36593.1          LLRCHESQGELSSAPEAPGTQEGPTCDGTPLPEPGTSELRDPLLMQLRPPPLSEPALAFVV
NP055586_RFP_40     LLRCHESQGELSSAPEAPGTQEGPTCDGTPLPEPGTSELRDPLLMQLRPPPLSEPALAFVV
AAK58539_RFP_20     ILKRYDLEQGLGDLLTER------KALVVPEPEPDSDSNQERKDDRERGEGQEPAFSFLA

TAIR_At2g44950      SSSNICSNQMEENGVNTSSQMTQTLYNLVAATEDLRCLKDELYPTVLRTNLGKDLCGQLA
CAD41603.3          SG-CLPGCHLGSDAPPLHLSTANALGDIFFPSSDLLQANEECALAALTKLPENDRSKQLQ
MIPS_At1g55250      SKSDEVVRKVEEALALRHSSTMELMGLFENTIDTQKTKAESISQSLHAVKSTEDATIQLS
NP922769.1          NDDSSLSKLVEEALALRYSTTVTLMKSLQEAFAVQQARSESLSLALNGQNSSEDVIVALE
AAP36593.1          ALGASSSEEVELELQGRMEFSKAAVSRVVEASDRLQRRVEELCQRVYSRGDSEPLSEAAQ
NP055586_RFP_40     ALGASSSEEVELELQGRMEFSKAAVSRVVEASDRLQRRVEELCQRVYSRGDSEPLSEAAQ
AAK58539_RFP_20     TLASSSSEEMESQLQERVESSRRAVSQIVTVYDKLQEKVELLSRKLNS-GDNLIVEEAVQ

TAIR_At2g44950      LS--ELESEIKSFRGDLDDVLVKFKSLSRELQSHRDADAKVRVDLKRIRGELEDEVVELQ
CAD41603.3          STSSNLLSSLNNVVQALSNLQLKHKQLAEDYQNQRDSSARKRAEHRRLKEELASAASELE
MIPS_At1g55250      SINDLMKEESKNLREMIDALHVRHKEHSEQIQAYISSHSTDQSELKHLKGQLEEIKAELE
NP922769.1          NHNDYLKEVVDNLRQAVSIINRKHEKYLDEIEAFKNNQSRELHEVKCLSGELEESMAELE
AAP36593.1          AHTRELGRENRRLQDLATQLQEKHHRISLEYSELQDKVTSAETKVLEMETTVEDLQWDIE
NP055586_RFP_40     AHTRELGRENRRLQDLATQLQEKHHRISLEYSELQDKVTSAETKVLEMETTVEDLQWDIE
AAK58539_RFP_20     ELNSFLAQENMRLQELTDLLQEKHRTMSQEFSKLQSKVETAESRVSVLESMIDDLQWDID

TAIR_At2g44950      QCNGDLSALRAERDATAGAFFP---VLSLGNKLATSDRERDKQRDLQDMETVLKELTVLA
CAD41603.3          ETNYKLAALKAQRDNTQGARIP---YPTLGNKNMPEDKE------------------LI
MIPS_At1g55250      ENRRKLITLKMQKDAACEGHVT---SPAIANGSLSPEKPVDKTK-LRELKDSIDEIKIMA
NP922769.1          ESRRKLAVLQLQTGGGSLMNTS---APNGVNGSVSTDKSSDKGMGWRDLKDAVEEAKTLA
AAP36593.1          KLRKREQKLNKHLAEALEQLNS-GYYVSGSSSGFQGGQITLSMQKFEMLNAELEENQELA
NP055586_RFP_40     KLRKREQKLNKHLAEALEQLNS-GYYVSGSSSGFQGGQITLSMQKFEMLNAELEENQELA
AAK58539_RFP_20     KIRKREQRLDRHLAEVLERVNSKGYKVYGAGSSLYGGTITINARKFEEMNAELEENKELA

TAIR_At2g44950      SGRLQQLKNLHEERTKMLGKMSNLQNKSK--SVRCISSSQACLSLKDQLEKSKEAVFQYM
CAD41603.3          SKRLVEIKRLHEERIEILNKIATFQNILM--DFKSIRSSKAFQLVNDRLQKSQAELDHYQ
MIPS_At1g55250      EGRLSELQASQEYNLSLSRQCQDIENELK--DDQYIYSSRLYSLINDRIHHWNAELDRYK
NP922769.1          ANRLFELHETQEDNLILSKQLEDIQDQLK--DENYIVTSKPYTILSDQLHHLNAEIERYR
AAP36593.1          NSRMAELEKLQAELQGAVRTNERLKVALRSLPEEVVRETGEYRMLQAQFSLLYNESLQVK
NP055586_RFP_40     NSRMAELEKLQAELQGAVRTNERLKVALRSLPEEVVRETGEYRMLQAQFSLLYNESLQVK
AAK58539_RFP_20     QNRLCELEKLRQDFEEVTTQNEKLKVELRSAVEQVVKETPEYRCMQSQFSVLYNESLQLK

TAIR_At2g44950      ALLEKLQVEKDSIVWKEREINIKNELGDVSRKTSAVTDSRMASLDSEIQKQLDEKMRIKT
CAD41603.3          TLLEKLQVDKDKFVWQERQFNLKVDLAEIPERVSTY----------------------
MIPS_At1g55250      ILTEAIQAERSFVMRRDKELNLRAESLEAANHKTTTVGSRIEVLEKKLQSCIIEKNGLEL
NP922769.1          GLVEVLQAK---------------------------IEDLEHEIQKLMAEKNDLEI
AAP36593.1          TQLDEARGLLLATKNSHLRHIEHMESDELGLQKKLR--TEVIQLEDTLAQVRKEYEMLRI
NP055586_RFP_40     TQLDEARGLLLATKNSHLRHIEHMESDELGLQKKLR--TEVIQLEDTLAQVRKEYEMLRI
AAK58539_RFP_20     AHLDEARTLLHGTRGTHQHQVELIERDEVSLHKKLR-TEVIQLEDTLAQVRKEYEMLRI

TAIR_At2g44950      RLGNISRE-RGRKEIFADMKALISSFPEEMSSMRSQLNNYKETAGGIHSLR---------
CAD41603.3          ----------CRNQVITKFKALVSSIPREMGAMQSEMTKHKEASLELNSLR---------
MIPS_At1g55250      ETEEAIQD-SERQDIKSEFIAMASTLSKEMEMMEAQLKRWKDTAQDALYLR---------
NP922769.1          KAEEALQD-SGKKDFKDEIHVMAASLSKEMELLDNQMNRSKDAASEALALR---------
AAP36593.1          EFEQNLAANEQAGPINREMRHLISSLQNHHQLKGDAQRYKRKLREVQAEIGKLRAQASG
NP055586_RFP_40     EFEQNLAANEQAGPINREMRHLISSLQNHHQLKGDAQRYKRKLREVQAEIGKLRAQASG
AAK58539_RFP_20     EFEQTLAANEQAGPINREMRHLISSLQNHNHQLKGEVLRYKRKLREAQSDLNKTRLRS-G

TAIR_At2g44950      --------------------------------------------------ADVQSLSGVLC
CAD41603.3          --------------------------------------------------AEVHSLSRILS
```

Fig. 10 (continued):

```
MIPS_At1g55250      ------------------------------------------------EQAQSLRVSLS
NP922769.1          ------------------------------------------------EEADYLRTLLA
AAP36593.1          SAHSTPNLGHPEDSGVSAPAPGKEEGGPGPVSTPDNRKEMAPVPGTTTTTTSVKKEELVP
NP055586_RFP_40     SAHSTPNLGHPEDSGVSAPAPGKEEGGPGPVSTPDNRKEMAPVPGTTTTTTSVKKEELVP
AAK58539_RFP_20     SALLQSQ---------SSTEDPKDE----PAELKPDSEDLSSQS-SASKASQEDANEIKS

TAIR_At2g44950      RKTKEYEALQLRSADYASQLGDLNATVCDLKNSHEELKLFLDMYKRESTDARDIAEAKEQ
CAD41603.3          RKERDNEEASCRSARAGSDITQLQSVISDLKQTNKELKLFADMYKRESTDSREIMESRDR
MIPS_At1g55250      NKADEQKGLEDKCAKQMAEIKSLKALIEKLLKEKLQLQNLASICTRECNDDRGLAEIKDS
NP922769.1          KK------------------IETLDQEKQELQFIVDMLGKECSESRAISEIEES
AAP36593.1          SEEDFQGITPGAQGPSSRGREPEARPKRELREREGPSLGPPPVASALSRADREKAKVEET
NP055586_RFP_40     SEEDFQGITPGAQGPSSRGREPEARPKRELREREGPSLGPPPVASALSRADREKAKVEET
AAK58539_RFP_20     KRDEEERERERREKERERERE---REKEKEREREKQKLKES-EKERDSAKDKEKGKHDDG

TAIR_At2g44950      EYRAWAHVQSLKSSLDEQN---------LELRVKAANEAEAVSQQMLA--AAEAEIADLR
CAD41603.3          EFLEWAHVHALKSSLDESK---------LEQRVKAANEAEAITQQRLA--TAEAEIAESG
MIPS_At1g55250      QRKAQAQAEELKNVLDEHF---------LELRVKAAHETESACQERLA--TAKAEIAELR
NP922769.1          ENRARKQAEYLRKCLEEHN---------LELRVKAANEAETACQQRLS--IAEAELEDLR
AAP36593.1          KRKESELLKGLRAELKKAQESQKEMKLLLDMYKSAPKEQRDKVQLMAAERKAKAEVDELR
NP055586_RFP_40     KRKESELLKGLRAELKKAQESQKEMKLLLDMYKSAPKEQRDKVQLMAAERKAKAEVDELR
AAK58539_RFP_20     RKKEAEIIKQLKIELKKAQESQKEMKLLLDMYRSAPKEQRDKVQLMAAEKKSKAELEDLR

TAIR_At2g44950      QKMDDCKR---------------------DVAKHSDILKSKHEEHGTYLSEIQTIGSA
CAD41603.3          QKLGTSRKYRIMLLNIVSLRTVEVGVTSLLGDLVSLSHMLKSKQEECEAYRVEVECIGQA
MIPS_At1g55250      TQLDLSER---------------------EVLELKEGIKVKEQEAEASIAEMETIGQA
NP922769.1          AKVDASER---------------------DVMKLKESIRIKEAEVDGHISEIETIGQA
AAP36593.1          SRIRELEERDRRESKKIADEDALRRIRQAEEQIEHLQRKLGATKQEEEALLSEMDVTGQA
NP055586_RFP_40     SRIRELEERDRRESKKIADEDALRRIRQAEEQIEHLQRKLGATKQEEEALLSEMDVTGQA
AAK58539_RFP_20     QRLKDLEDKEKKENTKMADEDALRKIRAVEEQIEYLQKKLAMAKQEEEALLSEMDVTGQA

TAIR_At2g44950      YEDIVPQNQQLLLQVTERDDYNIK--------------------LFLEGITS
CAD41603.3          YEDIQAQNQQLLQQIIERDDDNTKDVRFGYIVNLIVPETQYFIEKLFTCVKLIFMEGVKA
MIPS_At1g55250      YEDMQTQNQHLLQQVAERDDYNIK--------------------LVSESVKT
NP922769.1          YEDMQTQNQHLLQQVADRDDFNIK--------------------LVSDSVKM
AAP36593.1          FEDMQEQNGRLLQQLREKDDANFK--------------------LMSERIKA
NP055586_RFP_40     FEDMQEQNGRLLQQLREKDDANFK--------------------LMSERIKA
AAK58539_RFP_20     FEDMQEQNIRLMQQLREKDDANFK--------------------LMSERIKS

TAIR_At2g44950      RQMQDTLLIDKYIMDKDIQQGSAYASFLSKKSSRIEDQLRFCTDQFQKLAEDKYQKSVSL
CAD41603.3          KQTQDALHLETYSLRRNLQQESSLMDLYNQKIVSLEDQLKMWSDRVGKLQEDGWQQSVSL
MIPS_At1g55250      KHAYNTHLSEKQVMEKQLHQVNASVENFKARIAHNEEQMKGCFSEAYKLIQEDRHLVISL
NP922769.1          KQAYGSLLAEKNMLQKQLQHVNSSLESSKLKITSGEEQMKTYVAQAMKSSSENRHLAISL
AAP36593.1          NQIHKLLREEKDELGEQVLGLKSQVDAQLLTVQKLEEKERALQGSLGGVEKELTLRSQAL
NP055586_RFP_40     NQIHKLLREEKDELGEQVLGLKSQVDAQLLTVQKLEEKERALQGSLGGVEKELTLRSQAL
AAK58539_RFP_20     NQIHKLLKEEKEELADQVLTLKTQVDAQLQVVRKLEEKEHLLQSNIGTGEKELGLRTQAL

TAIR_At2g44950      ENLQKKRADIGNGLEQARSRLEESHSKVEQSRLDYGALELELEIERFNRRRIEEEMEIAK
CAD41603.3          SNYQRKLVDVHRDAQKLMQSLDGIQANVGSSRLEVADLLIELEKERFSKKRIEDDLEVMS
MIPS_At1g55250      ETTKWEVADADKEFRWLKSAVSSSEKEYEQISRRTDDIKLELDDER-EKKKLEEELMELN
NP922769.1          ERTMLEVSDAEKELKWLRSATGSAEKEYEINQKKIAELKMELERERNERIKLEEEYEEVK
AAP36593.1          ELNKRKAVEAAQLAEDLKVQLEHVQTRLREIQPCLAESRAAREKESFNLKRAQEDISRLR
NP055586_RFP_40     ELNKRKAVEAAQLAEDLKVQLEHVQTRLREIQPCLAESRAAREKESFNLKRAQEDISRLR
AAK58539_RFP_20     EMNKRKAMEAAQLADDLKAQLELAQKKLHDFQDEIVENSVTKEKDMFNFKRAQEDISRLR

TAIR_At2g44950      KKVSRLRSLIEGSSAIQKLRQELSEFKEILKCKACNDRPKEVVITKCYHLFCNPCVQKLT
CAD41603.3          RKASSLRAKARESAVLEKLRHEVKEYRGILKCGICHDRQKEVVITKCYHLFCNQCIQKSL
MIPS_At1g55250      KELEELGSES-VEAAIVRLQEEVKNCKNILKCGVCFDRPKEVVIVKCYHLFCQQCIQRSL
NP922769.1          NEVSELTSET-EETTIQKLQDEIKECKAILKCGVCFDRPKEVVITKCFHLFCSPCIQRNL
AAP36593.1          RKLEKQRKVEVYADADEILQEEIKEYKARLTCPCCNTRKKDAVLTKCFHVFCFECVRGRY
NP055586_RFP_40     RKLEKQRKVEVYADADEILQEEIKEYKARLTCPCCNTRKKDAVLTKCFHVFCFECVRGRY
AAK58539_RFP_20     RKLETTKKPDNVPKCDEILMEEIKDYKARLTCPCCNMRKKDAVLTKCFHVFCFECVKGRY

TAIR_At2g44950      GTRQKKCPTCSASFGPNDIKPIYI--
CAD41603.3          GNRQRRCPSCSLSFGANDVKPIYI--
MIPS_At1g55250      EIRHRKCPGCGTAFGQNDVRLVKM--
NP922769.1          EIRHRKCPGCTPFGQSDVREVKI--
AAP36593.1          EARQRKCPKCNAAFGAHDFHRIYISL
NP055586_RFP_40     EARQRKCPKCNAAFGAHDFHRIYIS-
AAK58539_RFP_20     DTRQRKCPKCNAAFGANDFHRIYIS-
```

MODULATION OF PLANT CELL NUMBER

The present invention relates to the use of the ANG4 gene, or a variant thereof, to modulate the cell number of a plant organ. Said modulation can be used to increase the plant biomass, or to adapt the plant architecture.

Plant architecture, especially leaf and root morphology, is an important factor in the determination of the plant productivity. Therefore, the study of genes involved in plant architecture and their regulation has drawn a lot of attention by several research groups.

The isolation, identification, characterization and manipulation of genes that are candidates for controlling leaf development is a key in understanding how plant leaves are constructed. Several methods have been used to study genes and their functions that regulate leaf development such as forward or reverse genetics. During leaf development processes, there are at least two factors that affect the leaf phenotype, at first cell division, that results in a given cell number, and second is cell expansion, which is required for the establishment of the cell size and shape. The length and width of leaves are regulated by cell division and cell expansion according to a gradient (Pyke et al., 1991; Van Lijsebettens and Clarke, 1998). In addition, the leaves are also modulated by environmental factors such as water, nutrients, light and $CO_2$ concentration. Berna et al. (1999) gives an overview of mutations and phenotypic classes that influence leaf morphology in *Arabidopsis*. Some of those mutations were characterized on gene level. Genes that regulate cell number along the width axis are DRL1 and SWP1 genes that act mainly on lateral growth of the lamina (Nelissen et al., 2003 and Autran et al 2002).

Although these genes might be used to modulate the plant biomass, there is still a further need for genes controlling plant architecture, especially for genes capable of controlling the cell number in specific plant organs.

In this invention, we studied a mutant with narrow leaves, angusta4, from the seed collection of Berna et al, (1999) and identified the causal gene, which we called ANG4. The mutant was originally created by EMS method (FIG. 1A). Molecular analysis surprisingly showed that the causal gene for the angusta4 mutation, which is located on chromosome 2, is a RING finger protein (Anami, 2004; Stone et al., 2005) with E3 ligase activity. This activity is related to protein degradation, but has never been linked to altered leaf morphology. The width and length of angusta4 laminas was compared to wild type (Landsberg erecta) (FIG. 1A). The data showed that total length lamina in the angusta4 leaves is significantly reduced compared to Ler. angusta 4 had narrow first leaf and shorter petioles than Landsberg. The epidermal and palisade cell area in the angusta4 (11 mm2) is smaller than in wild type (19 mm2) as well. Even more surprisingly, we found that that the phenotype of the leaf is due to a drastic reduction in the number of palisade cells. Moreover, we found that the same mutation has a dramatical effect on root growth too, making the gene an interesting tool for biomass modulation.

A first aspect of the invention is the use of a gene encoding a protein comprising SEQ ID No2 (TAIR_At2g44950, FIG. 10), or a functional fragment or variant thereof, to modulate the cell number of a plant organ, or a part thereof. Preferably, said gene is encoding a protein consisting of Seq ID No2. Gene as used here, refers to the coding sequence, which may be linked to its own promoter, but is preferably operably linked to a promoter which is not its own. Said promoter can be any promoter suitable for expression in plants. Preferably, said promoter is a strong promoter, such as, but not limited to the 35S promoter. "Gene" refers both to the genomic sequence (including possible introns) as well as to the cDNA derived from the spliced messenger, operably linked to a promoter sequence. Coding sequence is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

Operably linked refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence.

A variant as used here is a plant gene comprising a ring finger, with a homology with SEQ ID No 2 of at least 25% identities and/or 45% positives, preferably at least 35% identifies and/or 55% positives, more preferably at least 45% identities and/or 65% positives, even more preferably at least 55% identities and/or 75% positives, most preferably at least 65% identities and/or 85% positives, as measured by a protein-protein Blast search. Preferably, said variant has E3 ubiquitin protein ligase activity. Preferred variants are the *Oryza sativa* ANG4 homologues CAD41603 and NP922769, as listed in FIG. 10. Plant organs, as used here, comprise roots, stem, leaves and flowers. Preferably, said plant organ is a plant leaf and/or a plant root. Parts of a plant organ are, as a non-limiting example, the palisade cells of the leaves, or the lateral roots. One preferred embodiment is the use according to the invention, whereby the modulation of the cell number is used to modulate the leaf morphology. A functional fragment, as used here, is any fragment that still has the E3 ubiquitin-protein ligase activity.

Still another aspect of the invention is the use of a gene encoding a protein comprising, preferably consisting of SEQ ID No2, or a functional fragment or variant thereof, to modulate the root length. Preferably said gene, variant of functional fragment is overexpressed and said modulation is an increase in root length. Preferably, said gene comprises SEQ ID No1 (genbank NM_130060).

Another aspect of the invention is the use of a gene encoding a protein comprising, preferably consisting of SEQ ID No2, or a functional fragment or variant thereof, to increase biomass. Preferably, said increase of biomass is obtained by an overexpression of said gene, variant or functional fragment.

BRIEF DESCRIPTION OF THE FIGURES

A: Transversal sections at the widest location of expanded lamina of first leaves of wild type (Ler)-(top) and angusta4 (bottom). B: Mean value of palisade cell number in first leaves of angusta4 and the wild type (asterisk indicates statically significant difference). C: Cross section of wild type at the midvein (Adaxial surface is up). D: Close up of wild type vascular tissue. E: Cross section of angusta4 at the midvein (Adaxial surface is up). F: Close up of angusta4 vascular tissue. (V: vascular bundle; P: palisade cell; x: xylem; ph: phloem; I: inter cellular space). G, H, I: Morphological data of expanded leaves of ang4-1 mutant (A, B, C). Bars represent mean values and standard deviation. * means statistical difference at p<0.001 from the t test. Histological observations of expanded leaves of ang4 mutant and Ler

FIG. 6: Fine mapping of the ANG4 gene: The Figure indicates the map-based cloning strategy where a set of eight AFLP primer combinations was applied to 20 F2 individual mutants that indicated that the ANG4 mutation was located on chromosome 2 (blue and white pattern). Further application of AFLP marker SM33_202 and SM26_495 narrowed the ANG4 interval to 293 kb. Finally, InDel and SNP markers were used on a total of 1062 recombinants that delimited the ANG4 area to 27 kb at the bottom of chromosome 2 flanked by SNP markers CER458218 and CER458367. The 27 kb region contained 4 genes, one of which was the ANG4 candidate gene.

FIG. 7: Separation of PCR products of At2g44960 gene following amplification with two primer sets. Lane 1 contains a 1 kb molecular weight marker. Lane 2-7 contains PCR products from Ler At2g44960 gene while lane 8-13 contains PCR products from ANG4 At2g44960 gene. PCR products of lane 2, 3, 4, 8, 9, and 10 were amplified with primer combinations Defle 12 and Defle 13 while PCR products of lane 5, 6, 7, 11, 12 and 13 were amplified with primer combination: Defle 14 and Defle 15.

FIG. 8: Example of an alignment performed by CLUST-ALW 1.8. This alignment is between 2652 bp and 3873 bp part of the At2g44950 gene that was amplified by 5'CTCGC-CCATTGTTGTTTCAG3' (SEQ ID NO:3) and 5'AAT-TGCGGAAACCATGTTCC 3' (SEQ ID NO:4) primer combination. It clearly demonstrates the point mutation induced by EMS as a C was changed to a T generating a stop codon UAG. Aligned Ang sequence in FIG. 8 is represented in SEQ ID NO:47. Aligned Ler sequence in FIG. 8 is represented in SEQ ID NO: 48.

FIG. 9: ANG4 gene structure. Shown are the ANG4 candidate genes covering a 27 kb region on chromosome 2 and linked by CER458218 and CER458367SNP markers. The unspliced mRNA of ANG4 has 19 exons and 18 introns covering a region of 6298 bp while the full length cDNA covers a region of 2637 bp. EMS mutagenization caused a C to change to a T generating a stop codon at the end of exon 16 hence truncating the protein from 878 amino acids to 844 amino acids (Exons in blue boxes, and introns in orange boxes). Figure drawn to scale; for the candidate genes structure, 1 cm=2 kb and for the unspliced mRNA and the spliced mRNA, 1 cm=1 kb FIG. 10: An alignment of the ANG4 homologues in different species. The orange underlined sequence indicates the conserved RING finger motif. Conserved cystein and histidine residues are colored with red and blue colors respectively. At2g44950 is ANG4 sequence with 878 amino acid residues. At1g55250 is the ANG4 homologue on chromosome 1 in *Arabidopsis* with 899 amino acids. NP_55586 and AAK58539 are ANG4 homologues in human genome with 1001 and 975 amino acids respectively. CAD41603 and NP922769 are the ANG4 homologues in *Oryza sativa* with 883 and 789 amino acids respectively. TAIR_At2g44950 in FIG. 10 is represented in SEQ ID NO:2. AAP36593.1 in FIG. 10 is represented in SEQ ID NO:49. AAK58539 RFP 20 in FIG. 10 is represented in SEQ ID NO:50. CAD41603.3 in FIG. 10 is represented in SEQ ID NO:51. MIPS_At1g55250 in FIG. 10 is represented in SEQ ID NO:52. NP055586_RFP 40 in FIG. 10 is represented in SEQ ID NO:53. NP922769.1 in FIG. 10 is represented in SEQ ID NO:54.

EXAMPLES

Figure 1:
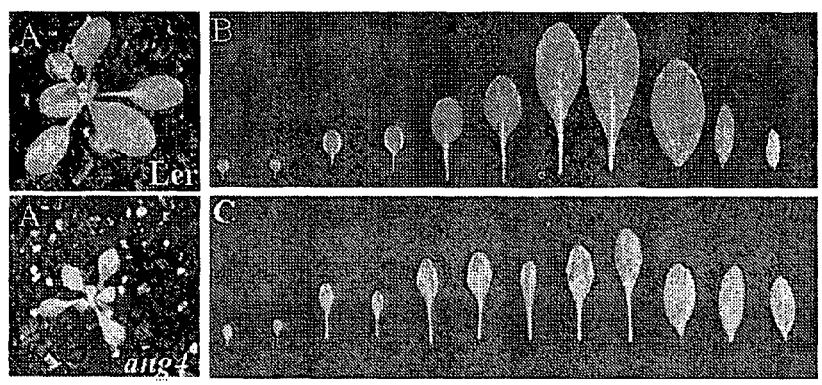
FIG. 1: Leaf phenotype of angusta4 and wild type. A: In vivo condition, fully grown rosettes of Ler and angusta4. B: Juvenile and adult fully expanded leaves of Ler. C: Juvenile and adult fully expanded leaves of angusta4.
Figure 2:
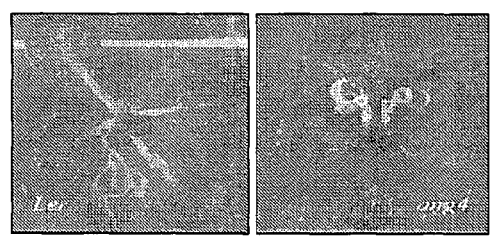
FIG. 2: In vitro leaf phenotype of wild type and angusta4 mutant plant (26 days after germination)

Materials and Methods According to the Invention

Plant Material and Growth Conditions

Seeds of the *Arabidopsis thaliana* (L.) Heynh. Landsberg erecta (Ler) and the ang4-2 mutant (SALK_122512) were obtained from the Nottingham *Arabidopsis* Stock Centre. The ang4-1 homozygous mutant was provided by J. L. Micol (Universidad Miguel Hernández, Alicante, Spain) (Berna et al., 1999). The T-DNA insertion line ang4-3 (GABI_276D08) was supplied from GABI-Kat.

Plants of the wild-type Landsberg erecta (Ler) and angusta4 (ang4) were grown in in vitro conditions with following conditions: 16/8 hrs (d/n) with white light (Neon tubes, cool white), 100 µEm$^{-2}$h$^{-1}$ PAR and 20° C. The medium was 2.15 g/l MS salts (micro and macro elements), 1 g/l sucrose, 0.5 g/l MES, pH 6.0, 6 g/l plant tissue culture agar. Seeds were sowed in 150×25 mm round dishes, sealed with Urgopore tape. Sixty seeds were sowed per plate. The vernalization period was 3 days after sowing.

For the root growth experiment, one lane of 5 plants were sowed in square plate in vertical position. The homozygous ang4-2 and ang4-3 lines were selected in in vitro medium containing kanamycin 25 mg/l for the ang4-2 or sulfadiazine 11.25 mg/l. for the ang4-3 line. The phenotype of the T-DNA insertion lines was scored in soil growth conditions.

Standard Leaf Analysis

Eight to twelve expanded first and third leaves of 30-days-old and 40-days-old Ler and ang4 in vitro grown plants have been harvested, treated with 100% methanol O/N, cleared with 90% lactic acid for 2-3 days O/N and put on a slide for image analysis. Petiole, lamina and leaf length, lamina width and area of first and third leaves have been measured with the Scion Image software (version β-3b; Scion Corp., Frederick, Md.) from digital pictures directly taken from binocular observations.

The statistical significance of the mean differences ($p \leq 0.05$) was analyzed by t-test using the SPSS (Statistical Package for the Social Sciences, version 10.0.5, SPSS, Inc.; Chicago, Ill.) software on normally distributed data.

Root Growth Kinetics 15 seeds of each angusta4 line was sown out (made only or one row per plates) in the square plates with GM medium contain vitamin. The plates were oriented in a vertical position. By using scalpel, roots of these lines were marked every two days until 14 days.

Differential Interference Contrast (DIC) Optic Analysis

The cleared first and third Ler and ang4 leaves prepared for the imaging analysis have been used to perform DIC (Differential Interference Contrast) optics analysis. This technique allows counting the number of cells of a determinate histological tissue layer and most importantly measuring the cell area from the adaxial side using a Scion Image.

Leaf Histology: Determination of Palisade Cell Number (PCN)

26 day-old fully expanded first and third leaves of Ler and angusta4 plants were harvested and immediately fixed in FAA (90% EtOH, 5% acetic acid, 5% formaldehyde) at 4° C. overnight. The process of dehydratation was done by increasing concentrations of EtOH as followed: 2×30 min EtOH 50%, 2 h EtOH 50%, 2 h EtOH 70%, 2 h EtOH 80%, O/N EtOH 80%, 2×2 h EtOH 90% and ultimately O/N EtOH 95%. Tissue infiltration was realized in a gradually permeation of Historesin and was achieved by first putting the leaves for 4 h in a mix of 50% EtOH and 50% Historesin, followed by another mix of 30% EtOH and 70% Historesin for 4 h and finally in 100% Historesin for 4 h. During that time, the samples were always kept for 30 min in vacuum. During the last step, the leaves were shacking at room temperature for 3 days. The leaves were then immerged in a new basic resin solution containing a 1% temperature-sensitive activator and left shaking ON. Leaves were finally oriented in beds which were half-filled with the resin solution, covered with new resin and left polymerizing at 45° C. for at least 2 h. The histology analysis has been performed on 5 μm sections collected on glass slides by using a Reichert Jung Ultracut Microtome using homemade glass knives. The Historesin leaf-containing blocks obtained after polymerization were oriented on a plastic cube and fixed with super-glue. The plastic cubes were holder by the micro tube climb.

Cytoplasm were stained in each sections by toluidin blue following the process below: The treated glass slides were stained for 8 min in 0.05% Teledyne blue and 0.1 M phosphate buffer, pH 6.8 for 10 minutes. After two washes (5 to 10 minutes each) in sterilize water, the slides were dried and mounted with DePex. Photographs were taken by using an Olympus CAMEDIA C-3040 digital camera zoom 3.3 mega pixel at the same magnification and pictures image were performed by Adobe Photoshop 6.0 program.

5 μm transversal sections of 28-day-old Ler and ang4 first and third full-expanded leaves have been made with a Reichert Jung Ultracut microtome in order to determine with the aid of a binocular microscope the Palisade Cell Number (PCN) present at the widest part of the lamina. This parameter is an indicator of leaf blade lateral growth (Tsuge et al., 1996). Several leaves have been entirely sectioned from tip to petiole: one section every ten has been collected and put on a glass slide. The glass slides were subsequently stained with toluidine blue and mounted with DePex.

Confocal Microscopy Observations of Root Meristem 7 days old seedling of angusta4 were stained with 100 ng/ml propidium iodide solution for 3 minutes and washed 3 times by sterilized water. Stained root were observed under a MRC600 Biorad confocal microscope using 543 nm excitation 560 LB light.

Flow Cytometry

The flow cytometry analysis was performed as described by De Veyider et al. (2001). The first two leaves were chopped with a razor blade in 300 μl of buffer (45 mM $MgCl_2$, 30 mM sodium citrate, 20 mM 3-[N-morpholino]propanesulphonic acid, pH 7, and 1% Triton X-100) (Galbraight et al., 1991). To the supernatant, which was filtered over a 30-μm mesh, 1 μl of 4,6-diamidino-2-phenylindole (DAPI) from a stock of 1 mg/mL was added. The nuclei were analyzed with the BRYTE HS flow cytometer, using Win-Bryte software (Bio-Rad, Hercules, Calif.). Of each time point, two biological and three technical replicates were taken.

Leaf Growth Kinematic Analysis

Leaf growth was analyzed kinematically from 5 to 28 days after sowing as described (De Veyider et al., 2001). The wild-type and ang4-1 plants were germinated and grown in in vitro conditions in GM+V medium. The following parameters were determined: total area of all cells in the drawing, total number of cells, and number of guard cells. From these data, we calculated the average cell area and estimated the total number of cells per leaf by dividing the leaf area by the average cell area (averaged between the apical and basal positions). Finally, average cell division rates for the whole leaf were determined as the slope of the $\log_2$-transformed number of cells per leaf, which was done using five-point differentiation formulas (Erickson, 1976).

Map Based Cloning Procedure

The DNA extraction, AFLP, insertion/deletion (InDel) and single-nucleotide polymorphism (SNP) analysis were done according to (Peters et al., 2004) and (Cnops et al., 2004). A standard set of 8 AFLP markers were analyzed on 20 $F_2$ mutants and identified the mutation in a 493 kb interval on chromosome 2. The fine-mapping of the ANG4 locus was done using the InDel and SNP markers described in Table SI. Recombinants were used for fine-mapping and delineated the locus to 97 and 27 kb regions flanked by SNP markers. The last interval covered a 27 kb region between CER458218 and CER458367SNP markers and contained 4 genes that were sequenced.

The candidate genes identified in the last mapping interval were amplified from DNA and cDNA, and fully sequenced in at least 3 replicates to identify the base exchange in the ang4-1 mutant compared to Ler.

Microarrays Experiment

The studied organs, shoot apex of plants (comprising shoot apex meristem, first and second rosette leaf primordia at petiole-less stage), were harvested removing the cotyledons and the hypocotyls. The harvesting was done in the laboratory conditions under additional light and 20° C. between 11 am and 6 pm. The age of the plants at the harvesting step were between 8 and 15 days after germination depending of the delay of mutant development. RNA were extracted with TRIzol Reagent (Life Technologies, Breda, The Netherlands). The experimental design comprised 3 replicates of Ler and ang4, one replicate corresponding to one RNA extraction and about 150 apexis.

Microarrays experiment was done by the VIB Microarrays Facility lab (Paul van Hummelen, Leuven, Belgium; worldwideweb.microarras.be/) using ATH1 Affymetrix chips of 23,800 probes sets for *Arabidopsis thaliana*. The raw data were normalized and summarized using Robust Multi-Array average method from affy package of Bioconductor statistical R programs (Wu and Irizarry, 2004). The genes were ranking in order of evidence for differential expression DE between mutant and wild type using an empirical Bayes method performed with the limma package of Bioconductor. This method consists to combine at the gene level with means and standard deviation from the 3 replicates to form a statistic B which is a Bayes log posterior log-odds that each gene is DE (Lonnstedt and Speed, 2002; Smyth et al. 2003). The p value calculating from B data was corrected by Holm's method and the cut-off value of p was 0.01.

Alleles Characterization

The ang4-2 and ang4-3 mutants with T-DNA insertion respectively in the exon 6 and the exon 19 of ANG4 gene were studied (worldwideweb.arabidopsis.org). The T-DNA insertion was checked by PCR on F2 plants using primers designed before (P1) and after (P3) the putative position of the T-DNA and a primer specific of the left border of the T-DNA (P2). A positive amplification between P1 and P2 validates the position of the T-DNA insertion. A coincident positive or negative amplification using P1 and P3 shows that the line is respectively heterozygous or homozygous.

Over-Expression Construct and Plant Transformation

To obtain overexpression lines of ANG4 the open reading frame (including ATG and stop codon) of ANG4 (2637 bp) was amplified by Pfu polymerase and cloned into the pDONRT221 vector using the GATEWAY recombination strategy (Invitrogen) to obtain ENTRY clones. The ENTRY clone was recombined with the pK7WG2 vector (Karimi et al., 2002) to obtain a DESTINATION vector with the ORF under the control of a 35S promotor. This construct was introduced into *Agrobacterium tumefaciens* and subsequently Ler or ang4-1 plants were transformed with the *Agrobacterium tumefaciens* suspension through floral dip. The $T_0$ seeds were grown in high density on growth medium containing Kanamycin (50 μg/ml), Nystatin (50 μg/ml) and Carbenicillin (250 μg/ml) to select the transformants. These $T_1$ transformants were transferred to soil to obtain $T_2$ seeds.

Example 1

Histological Analysis of the Ang4 Mutation

We performed an anatomical analysis in the first leaf by using light microscopy to identify phenotypic functions of the ANGUSTA 4 gene. Our interest was to focus on the number of palisade cells, structure of vascular tissue in the leaf as well as primary root development of mutant plants in comparison with that of wild type.

We looked at the anatomy of angusta4 leaves to determine whether cell division or cell expansion was affected and to check polarity and studied root growth kinetic as a measure for root apical meristem activity in the mutants. In plant, cell expansion and cell division are key parameter in the determination of organ shape.

Figure 3:
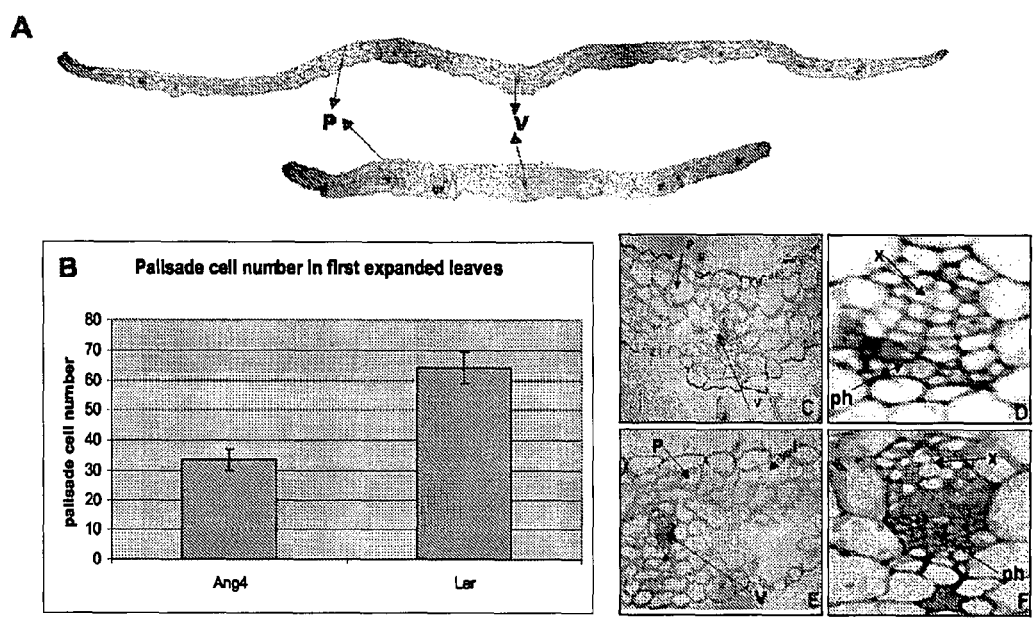
FIG. 3: Leaf phenotype of angusta4
Figure 3G:
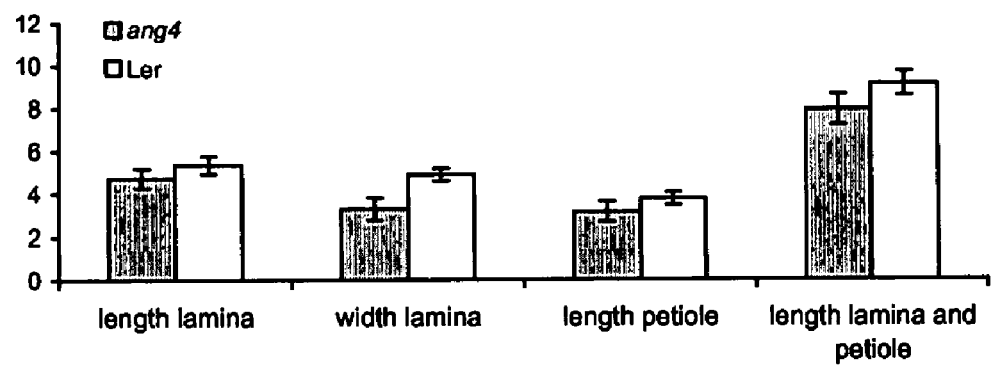
Figure 3H:
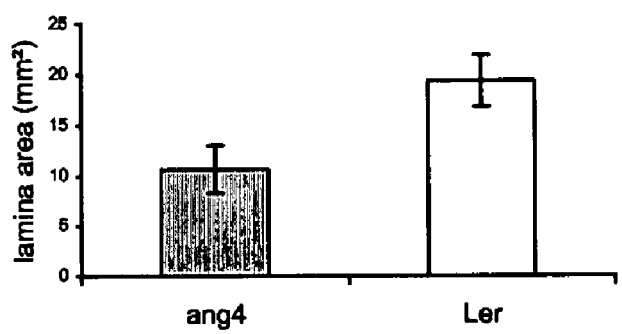
Figure 3I:
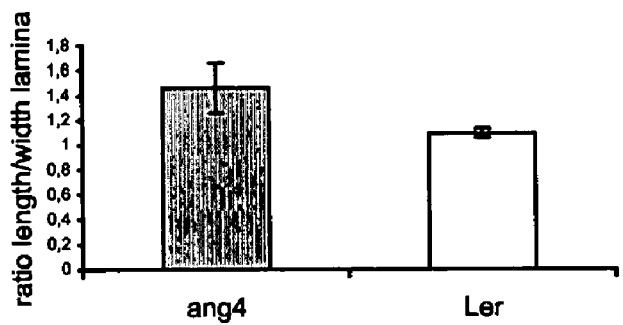
Figure 4A:
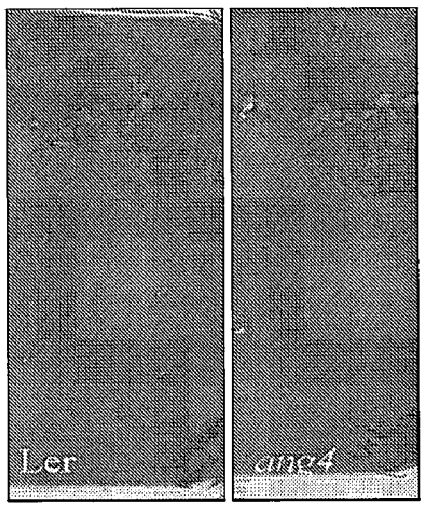
FIG. 4**: A: In vitro root growth after 15 days of germination. B: Biomass of ang4-1, ang4-2, ang4-3 mutants, Ler and Col in soil conditions. Average of 2 assays, 4 blocks per assay and 8 plants per block. The bars correspond to the standard deviation.
Figure 4B:
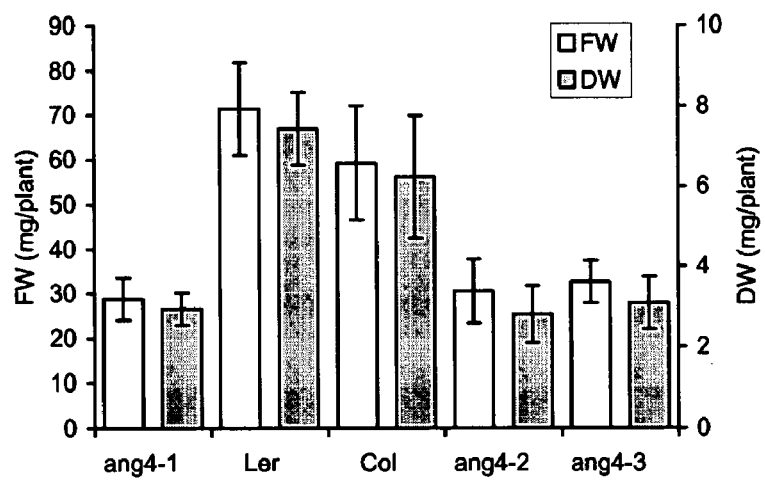

Major trait of the angusta class of mutants is narrow leaf lamina (Berna et al., 1999; FIG. 1). The reduced leaf size in ang4-1 mutant was confirmed by morphological measurements of expanded leaves. The measurements showed a significant decrease of lamina length and width, petiole length and total lamina and petiole length (FIG. 3G). The lamina area of ang4-1 first and second expanded leaves was 10.7±2.4 $mm^2$ i.e. 55% of Ler lamina area which was 19.3±2.5 $mm^2$ (FIG. 3H). The length/width ratio of the lamina was significantly increased in ang4-1 mutant showing a modification of the lamina proportions and to a narrower shape (FIG. 3I). The fresh weight of the rosette leaves at the flower emergence stage of development were significantly reduced in ang4 mutants: ang4-1 biomass was 40% of Ler biomass, and ang4-2 and ang4-3 fresh weight were respectively 51% and 55% compared to Col (FIG. 4B). The dry weight was also strongly affected by the mutation in ANG4 with 39% for the ang4-1 plants compared to Ler, and respectively 45% and 49% for the ang4-2 and ang4-3 plants compared to Col.

Serial sections through historesin embedded expanded first leaves (26 day old seedlings) were taken (FIG. 3A). The number of palisade cells was counted in a number of serial sections at the widest width of the leaf to be used as a measure for lateral growth of the leaf lamina (Tsuge et al 1996). The number of palisade cells of angusta4 was smaller than wild type. The data showed that the number of palisade cells is 30 in the angusta4, and about 66 cells in Ler (FIG. 3B). Thus, palisade cells were reduced by about 50% in angusta4 compared to wild type. The structure of palisade cell was larger and distributed more irregularly than in Landsberg (FIGS. 3C & E).

The vascular tissue of Ler wild type and angusta4 mutants was also visualized under the microscope. The polarity was correct in the mutant: xylem at the dorsal side and phloem at the ventral side. The midvein of wild type and mutant are shown (FIG. 3D-F). In the angusta4 mutants, cells surrounding xylem and phloem were bigger than in Ler. The number of cells is also higher in the vascular bundle in the angusta4 midvein (FIGS. 3 E and F). These data show that the ANGUSTA4 gene is involved in the regulation of cell number during leaf growth; it has no function in leaf polarity.

Figure 5:
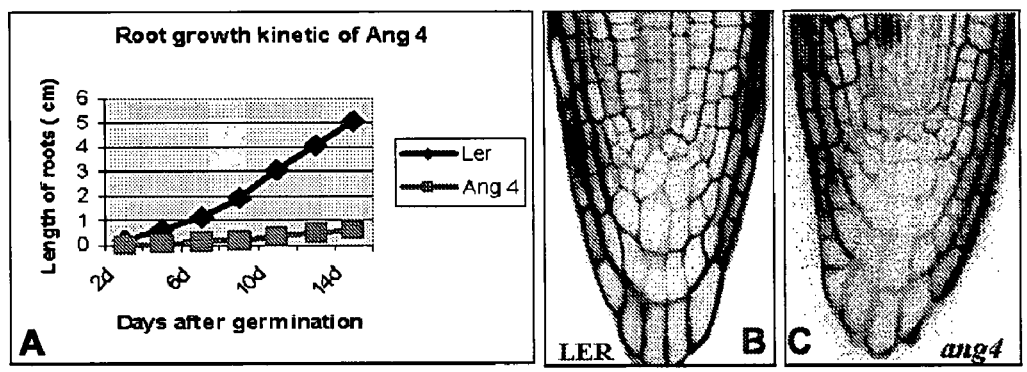
FIG. 5: A: Root growth kinetics of angusta4 in comparison with wild type (Ler). B and C: Longitudinal sections by confocal microscopy through the root apical meristem in the root tip in wild type and the angusta4 mutants.

To investigate in more detail the function of the ANGUSTA4 gene, primary root growth was analysed. 60 seedlings of angusta4 and Ler were germinated in the square plates and kept in vertical position in the tissue culture room. The root tip was marked every 2 days with a scalpel blade. The mean value was calculated for each time point. A graphical representation of these mean values is shown in FIG. 5A. After 15 days, the length of angusta4 reached 1 cm, which is much shorter than the 5 cm of the Ler line. In addition, angusta4 roots started to form adventitious roots after four days germination; each angusta4 plant had 2 to 3 adventitious roots.

Moreover, apical sections from in planta *Arabidopsis* roots (7 days old seedling and n=20) were visualized under confocal microscope to investigate the structure of the root apical meristem. FIGS. 5B and C showed the meristem zone of the primary root in angusta4 and wild type. Longitudinal section of root meristem region of angusta4 showed no difference in cell division and cell expansion. It indicates no defective root meristem activity.

The flower organization is also altered by ANG4 mutation. The floral diagrams of ang4-1 showed an asymmetric position of the petals and missing anther or carpel. The flower of ang4-2 and ang4-3 plants was not modified but the inflorescence stem appeared thinner as compared to Col. To verify if ang4 mutation only affected aerial organs, the root growth rate was analysed and compared to Col alleles and wild types. The root growth was strongly decreased in ang4-1 plants compared to the wild type Ler. However, the root growth of ang4-2 and ang4-3 was similar to that of the wild-type Col suggesting that the mutation of ANG4 gene does not alter the root growth in the genetic background of Col.

Thus, the ANG4 gene has a function in leaf and flower development and root growth.

Example 2

Mapping of ANG4 Leaf Form Mutation

The mutant, ang4, was obtained from the collection of 255 mutant lines induced by EMS mutagenesis (Berna et al., 1999). The aim of this work was to verify the ANG4 region delimited by AFLP, InDel and SNPs markers and by recombinant analysis. The Ler mutant was crossed with Col-0 wild type and the resulting F1's were allowed to self in order to produce F2 mapping populations (Robles and Micol., 2001). 320 F2 mutants together with their Ler and Col-0 parents were analyzed using a standard set of eight AFLP primer combinations shown in Table 1 in order to visualize 85 AFLP markers on the genome (Peters et al., 2004). After scoring the resulting 85 AFLP markers, linkage to chromosome 2 and non-linkage to other chromosomes was observed. Table 2 shows the genotypic scoring that was done using AFLP, InDel and SNP markers. Presence of the AFLP marker signifies that the marker behaves as the Col parent and is represented in Table 2 as number 1. For the F2 individuals this means that the marker is either homozygous or heterozygous. Absence of the AFLP marker indicates that the marker is homozygous Ler and it is indicated as number zero (0) in Table 2.

Initially, as shown in Table 2, F3 recombinants 670, 227, and 1389 were scored as homozygous mutants (100% ang4) while recombinants 635, 1472, 1747 and 387, 1607,1716 were scored as heterozygote (1 ang4: 3 wild type) and homozygote (100% Ler) respectively. During meiosis, for recombinant 1747, a cross-over event took place between markers CER458218 and CER442324. This recombinant was used to delimit ANG4 mutation from the top of chromosome 2 and hence marker CER442324 was taken as the top marker that limited the ANG4 interval. In contrast, a cross over event occurred between markers CER458218 and CER458219 for recombinant 670 and 227, markers CER442324 and CER458218 for recombinant 1389 and markers CER442323 and CER458367 for recombinants 1472. All these markers delimited the ANG4 mutation from the bottom of chromosome 2. Delimiting the ANG4 region became rather difficult because the mutant was phenotypically very clear in the Ler background and less clear after crossing (i.e., it was difficult to score the phenotype in the F2 derived F3 populations).

In order to verify the ANG4 interval of 27 kb, and probably reduce this region to about 10 to 20 kb, phenotypic scores of the F3 of nine recombinants that were not very informative in the previous scoring were repeated. In vitro, thirty seeds of each recombinant were planted on GM medium in 150×25 mm Petri dishes in replicate. 200 seeds of each recombinant were planted in vivo on trays containing 52 wells in which one seed was planted in each well. Phenotypic scores were done at four time points over a period of 4 weeks to determine whether the F3 was homozygous mutant (100% ang4), heterozygous (1 ang4: 3wild type) or homozygous wild type (100% wild type Ler) and these scores are summarized in Table 3, and compared to the previous less extensive scoring. Recombinants 635, 670, and 1389 were scored differently compared to previous scoring.

Earlier phenotypic scores had shown that recombinant 635 was heterozygote while recombinants 670, 1385, and 1472 were homozygote mutant. Table 3, which indicates new phenotypic scoring, revised these earlier scores. Recombinant 227 was very difficult to score in the second round of phenotype scoring, as it was less clear in vitro. Scores from in vivo growth conditions indicated that it was homozygous mutant.

For instance, recombinant 670 was scored as a homozygous mutant before and from Table 3, it was scored as heterozygous (1 mutant: 3 wild type). It was therefore decided that a number of recombinants that were not clearly scored and therefore not very informative, including recombinants 387, 670, 1389, 1607 and 1716 would be ignored and that recombinants that were clearly scored as shown in Table 4 will be used to delimit the ANG4 mutation. As indicated in Table 4, the SNP marker that delimited ANG4 mutation from the top of chromosome 2 was CER458218 based on recombinant 227 while marker CER458367 delimited ANG4 mutation from the bottom of chromosome 2 based on recombinant 1472. These markers are within a 27 kb (26,647 mb) region. This region was the minimal region delimited by markers while the maximal ANG4 region was between CER458219 as the top marker based on recombinants 377 and 1775 and CER458367 as the bottom marker based on recombinant 1472. Recombinant lines that were most informative were those with Ler scoring because Col-0 is a recombinant inbreed line (RIL) and as such any cross over event in it does not necessarily indicate linkage to the mutation of interest as shown in Table 4 for recombinant 635.

Verification of the ANG4 mutation after the phenotypic scores showed that, indeed the ANG4 mutation was within the 27 kb region delimited by genotypic scoring as indicated in Table 2 and FIG. 6. Within this 27 kb region; there are 4 intact genes one of which has to be ANG4 gene.

The ANG4 interval was determined at 27 kb and flanked by CER458218 and CER458367 markers. This was based on the recombinant analysis of 1062 F2 plants. We checked the phenotypic region of the remaining recombinants in the F3 generation both in vivo and in vitro at 4 time points over a period of 4 weeks. The ANG4 region was determined and allowed to deduce the F2 genotypes. This F2 genotypic information was integrated in Table 4 and the ANG4 interval delineated to a 27 kb region containing 4 intact genes one of which has to be ANG4 gene.

Example 3

Sequencing of Candidate ANG4 Genes

Four candidate genes are situated in the 27 kb interval delimited by the recombinant analysis and are listed in Table 5 with their respective functions. For each gene, the genomic DNA was amplified from the ang4 mutant and compared to the wild type Ler in order to determine the single base change.

Total genomic DNA from ang4 mutant and Ler were extracted using the CTAB method and DNeasy Plant mini kit. Ler DNA acted as a control. For ang4 mutant, four candidate genes were amplified by performing three independent PCR for each of the primer combinations (Table 9). The same primer combinations were used to three independent PCR to amplify the four genes present in the genomic DNA of Ler. Primer pairs were designed for all the candidate genes that amplified overlapping segments of 800 bp-1200 bp spanning the entire 27 kb region (FIG. 6; Table 9). Three independent PCR reactions of these segments were sequenced. An example of this PCR amplification is shown in FIG. 7 where each band indicates DNA amplified with two primer sets. Sequence alignment was performed by CLUSTALW 1.8 software and compared with that of the wild type plant Ler. An example of sequence alignment is shown in FIG. 8 with the gene At2g44950. Sequencing of these fragments and comparison with the wild type Ler sequence identified a missense change in the candidate gene At2g44950 generating a stop codon UAG instead of the CAG codon corresponding to amino acid glutamine in the predicted exon 16 (FIG. 9). Sequence alignment of other candidate genes, At2g44940, At2g44970 and At2g44980 genes did not show any mutation.

The At2g44950 gene is within the 27 kb region on chromosome 2 together with At2g44940, At2g44970 and At2g44980 genes flanked with CER458218 marker from the top of chromosome 2 and CER458367 marker from the bottom of chromosome 2 as shown in FIG. 9. Amongst these candidate genes, ANG4 is the largest covering a region of 6298 by with an open reading frame (ORF) of 5245 bp; while the At2g44940, At2g44970 and At2g44980 genes covers 1157 by with an ORF of 887 bp, 3337 by with an ORF of 3020 by and 4230 by with the same number of base pairs as its ORF respectively. ANG4 gene has two untranslated regions, one at the 5' end covering a region of 344 by and the other at the 3' end with 307 bp. It consists of 19 exons and 18 introns. Once the introns have been spliced, the exons form the full length cDNA that consists of 2637 by and this is translated in a protein of 878 amino acids (worldwideweb.arabidopsis.org).

The mutation that was found in the At2g44950 gene (FIG. 8), truncated the protein from 878 to 844 amino acids. This was as a result of the stop codon, UAG that was created at position 5183 in the unspliced mRNA and at position 2134 in the spliced mRNA when cytosine nucleotide changed to a tyrosine nucleotide that was caused by an EMS mutagenesis.

The At2g44950 gene has a RING-finger motif that begins with the amino acid cystein at position 826 in the amino acid sequence and ends with amino acid cystein at position 864 (CKACNDR-PKEVVITKCYHLFCNPCVQK-LT-GTRQKKCPTC) as shown in FIG. 10 SEQ ID NO:2. 18 amino acids of the RING finger motif are part of the 844 amino acids that makes a protein after the mutation and 23 amino acids of the RING finger motif are lost (FIG. 9). This means that the RING finger motif that functions as part of the E3 ligase was inactivated in the ang4 mutant and that this might have lead to defect in the degradation of a number of proteins in the proteasome.

Molecular cloning of ANG4 demonstrates that map-based cloning using AFLP markers is a reliable strategy for accessing genes from the genome of *Arabidopsis thaliana*. Cloning of ANG4 will facilitate studies on its function for crop improvement.

Example 4

ANG4 Homologues and Functional Domain

Data base searches revealed the presence of At2g44950 homologues as uncharacterized cDNA or open reading frames obtained from genome projects in a number of organisms including *Arabidopsis thaliana*, humans, and rice. ANG4 has a close homologue in *Arabidopsis thaliana* located on chromosome 1 (At1g55250). Sequence comparison analysis indicates that NP_055586 is the human orthologue of the *Arabidopsis* ANG4 The human genome also contains a second ANG4 homologue, AAK58539 (RING finger protein 20), which is encoded by a gene that is distinct from the NP_055586 gene (RING finger protein 40). In *Oryza sativa* (japonica cultivar-group), there appears to be two ANG4 homologues with accession numbers CAD41603 and NP922769. FIG. 10 shows an alignment of the amino acids of ang4 mutant and its homologues in humans, *Arabidopsis* and rice which revealed a conserved Really Interesting New Gene motif (RING finger) at the end of the sequences indicating that ANG4 is an evolutionary conserved protein. The RING finger domain has been classified into 20 different subgroups in *Arabidopsis thaliana* (Stone et al., 2005). In this sub groups, ANG4 was classified as having an ATP binding domain. We searched for this ATP binding domain (the P-loop) using Prosite (worldwideweb.expasy.org/cgi-bin/prosite/S and was not found though the ANG4 homology to ATPases involved in chromosome segregation and cell division was found. Search for other functional motifs was done but no other functional domain was found besides the RING finger.

Example 5

Alleles in ANG4

A number of alleles for At2g44950 gene with T-DNA insertions are available from Signal (signal.salk.edu/cgi-bin/tdnaexpress?GENE=at2g44950&FUNCTION=&TDNA=) and GABI ((worldwideweb.mpiz-koeln.mpg.de/GABI-Kat/db/search.php?type=seq&term=60-K015154-022-276-D08-8409) collections. T-DNA insertion lines are also available for the ANG4 homologue in *Arabidopsis* (At 1 g55250) (Table 6 A and B).

Example 6

ANG4 Expression Patterns in Different *Arabidopsis* Organs

Figure 11:
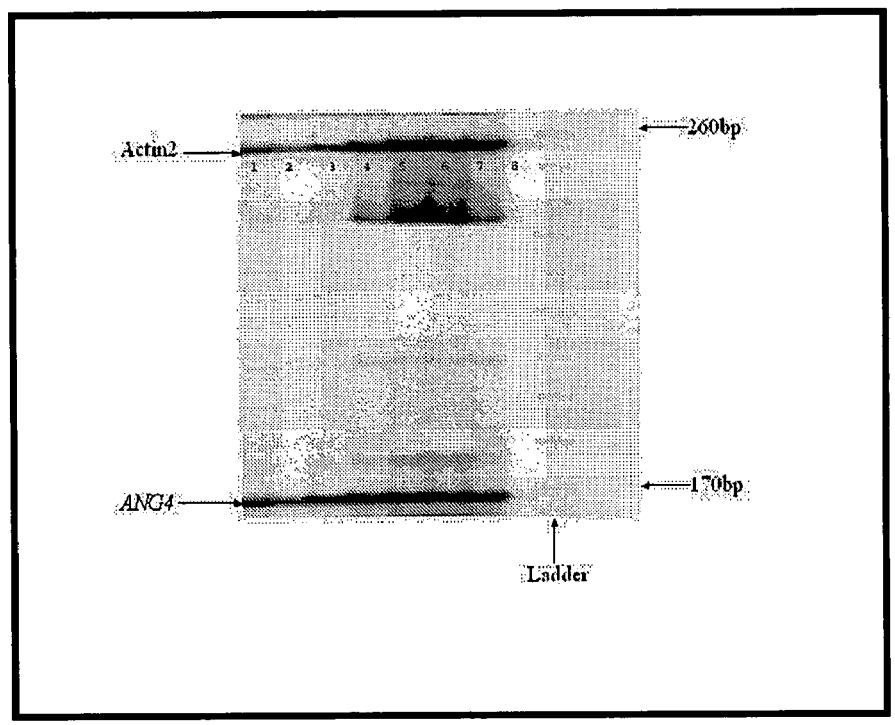
FIG. 11: RT-PCR analysis of ANG4 gene expression in different Ler organs. The expression pattern was visualized on acrylamide gel. 4 µl samples were loaded an acrylamide gel in 1× Tris-Boric acid-EDTA buffer and electrophoresed at 3000V. Primers Defle 44 and syana_01 were labeled with $P^{33}$. Numbers on the gel indicate different Ler organs as follows: 1—Ler apex, 2—Ler shoot apex, 3—Ler roots, 4—Ler cotyledons, 5—Ler young leaves, 6-Ler Expanded leaves, 7—Ler flowers and 8—water as a control sample.

To examine the expression pattern of ANG4 gene in Ler organs, we performed semi-quantitative reverse transcriptase (RT)-PCR analysis with different tissues including shoot apex, flower, young leaves, expanded leaves, cotyledon and roots. RNA was extracted from different frozen ground Ler organs using TRIZOL reagent (Life Technologies, Paisley, UK) according to manufacturer's protocol. The cDNA samples were standardized on actin transcript (At3g18780) amount using primers Defle 44 and Defle 45 with the following sequences: TGCTGGACGTGACCTTACTG (SEQ ID NO:5) as a forward primer and GGGCTGGAACAAGACT-TCTG (SEQ ID NO:6) as a reverse primer. The melting temperature for these standard primers that acted as control in this experiment was 59° C. for both. For ANG4 gene, the following gene specific primers were used: syana_01 as a forward primer and syana_02 as a reverse primer with the following sequences: TGCTCGAATCAGATGGAAGA (SEQ ID NO:7) and AGCTAGCTGACCGCACAAAT (SEQ ID NO:8) respectively. The melting temperature for syana_01 was 59° C. while for syana_02 was 60° C. Actin is a fundamental component of the cytoskeleton in all eukaryotes and directs the spatial organization of many crucial sub cellular processes. Hightower and Meagher (1986) proposed that the six subclasses of actin have been conserved during vascular plant evolution and hence it can be used as a reference for expression analysis of other plant genes. FIG. 11 shows the result of a typical RT-PCR analysis of the expression pattern of ANG4 in different Ler organs. Primers Defle 44 and Defle 45 amplified a single 253 by actin PCR product while primers syana_01 and syana_02 amplified a predicted single 164 by ANG4 PCR product. This analysis shows that the ANG4 gene is expressed in all organs studied.

The expression pattern of ANG4 gene in all Ler organs studied could indicate that it may play a basic role in all these organs. The understanding of whether ANG4 gene may be involved in other possible roles, it would be important to investigate its expression levels in response to hormone and stress treatment. In addition, the expression analysis at the cellular level will be analyzed using the GFP marker line. Expression of At2g44950 gene in all organs means that it is required for fundamental or basic processes in all plant organs and throughout the life cycle. Cellular experimental analysis would also indicate whether ANG4 gene function is related to cell division processes.

Example 7

Genome Wide Expression in ang4 Shoot Apex

Figure 12:
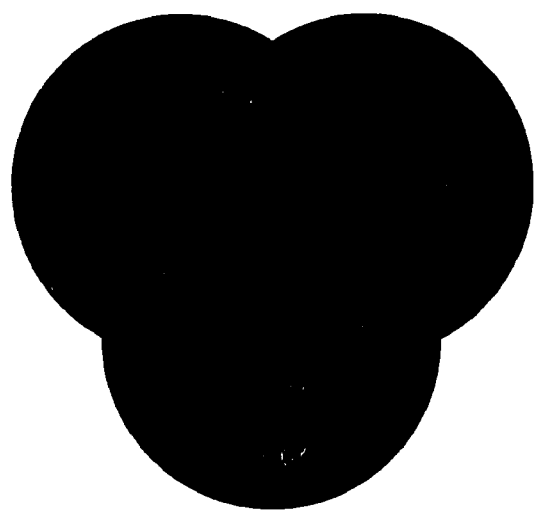
FIG. 12: Summary of *Arabidopsis* genes with altered mRNA expression in ang4 and two other leaf development mutants, elo2 and drl1-2. RNA was extracted from shoot apex of young plants and expression measured using ATH1 microarrays (Affymetrix) method in triplicates. Comparisons of expression level were done between each mutant and the wild-type Ler following the Bayesian test of linear model performed with Bioconductor programs. Values without parenthesis are the number of DE genes equally expressed in different mutants, and values in parenthesis, the number of DE genes up-regulated in one mutant and down-regulated in another.

A total of 1821 genes were differentially expressed (DE) in the apex of young plants of ang4 compared to Ler, that represents 8% of the *Arabidopsis* genome. Comparing these results with those obtained in other narrow leaf mutants (elo2 and drl1-2 involved in independent process to ang4), 1314 genes appeared differentially expressed specifically in ang4 (FIG. 12). Considering the level of expression, 494 genes are DE at a 2-fold change expression threshold. The number of genes regulated by ANG4 is higher than those regulated by the DRL1 and ELP1 genes, respectively mutated in drl1-2 and elo2 mutants, showing the general function of ANG4 in the development.

Most of the genes regulated by ANG4 are involved in cytokinesis and cell cycle. A partial list of the DE genes in ang4 shows that 24 cell cycle genes and 27 microtubule and myosin related genes, are regulated in ang4 mutant (Table 7). Among these, one finds 8 genes related to E2F-DP complex regulating the G1 to S transition in plants (De Veyider et al., 2003). Eight A- and B-type cyclins genes and 3 B-type cyclin-dependent kinase genes involved in G2 to M transition in cell cycle are down-regulated in ang4 genotype. Kinesins represent a super-family of microtubule motor proteins involved in the transport of vesicles and organelles, spindle formation and elongation, chromosome segregation, microtubule dynamics and morphogenesis (Reddy and Day, 2001). Among the 61 kinesin genes identified in *Arabidopsis* genome, 19 are down-regulated in ang4, that TETRASPORE involved in the formation of tetrad of microspores after meiosis (Yang et al., 2003). The HINKEL gene, another kinesin, plays a role in the reorganization of phragmoplast microtubules during cell plate formation (Strompen et al., 2002). Other cytokinesis related genes are also DE in ang4, as the cytoskeletal components actin 8, tubulins, myosin like proteins and microtubule-associated proteins. The PLEIADE gene that has a function in the stabilization of cytokinetic structures of cell plate during cytokinesis is also down-regulated in ang4 mutant (Muller et al., 2002). The KNOLLE gene, a cell-cycle-regulated syntaxin involved in membrane fusion in cytokinesis, is also repressed in ang4 (Muller et al., 2003). The SIAMESE gene, required for coordinating cell division and cell differentiation during the development of trichomes and may function as a repressor of mitosis in the endoreduplication cell cycle, is up-regulated in ang4. These results suggest an implication of ANG4 gene in cell cycle regulation.

Some genes related to plant development are also regulated by ANG4 gene expression (Table 8). The GLABRA1 gene is a MYB transcription factor that specify the primary cell fate during development of epidermal hairs in *Arabidopsis* (Schiefelbein, 2003). The homeobox genes KNAT2 and KNAT6 have a role in meristem initiation and maintenance (Tsiantis and Hay, 2003). The genes NAM and AINTEGUMENTA are known to be involved in organ initiation and separation (Traas and Vernoux, 2002). In *Arabidopsis*, SCARECROW (SCR) is essential for the asymmetric division of the cortex/endodermis progenitor cell in the root (Kamiya et al 2003). Two genes related to auxins are DE in ang4: a putative ARF1 auxin responsive transcription factor and a putative AUX1-like permease, a regulator of root gravitropism (Liscum and Reed, 2002).

Example 8

Effect of ang4 Mutation on Endoreduplication and Cell Expansion

Figure 13:
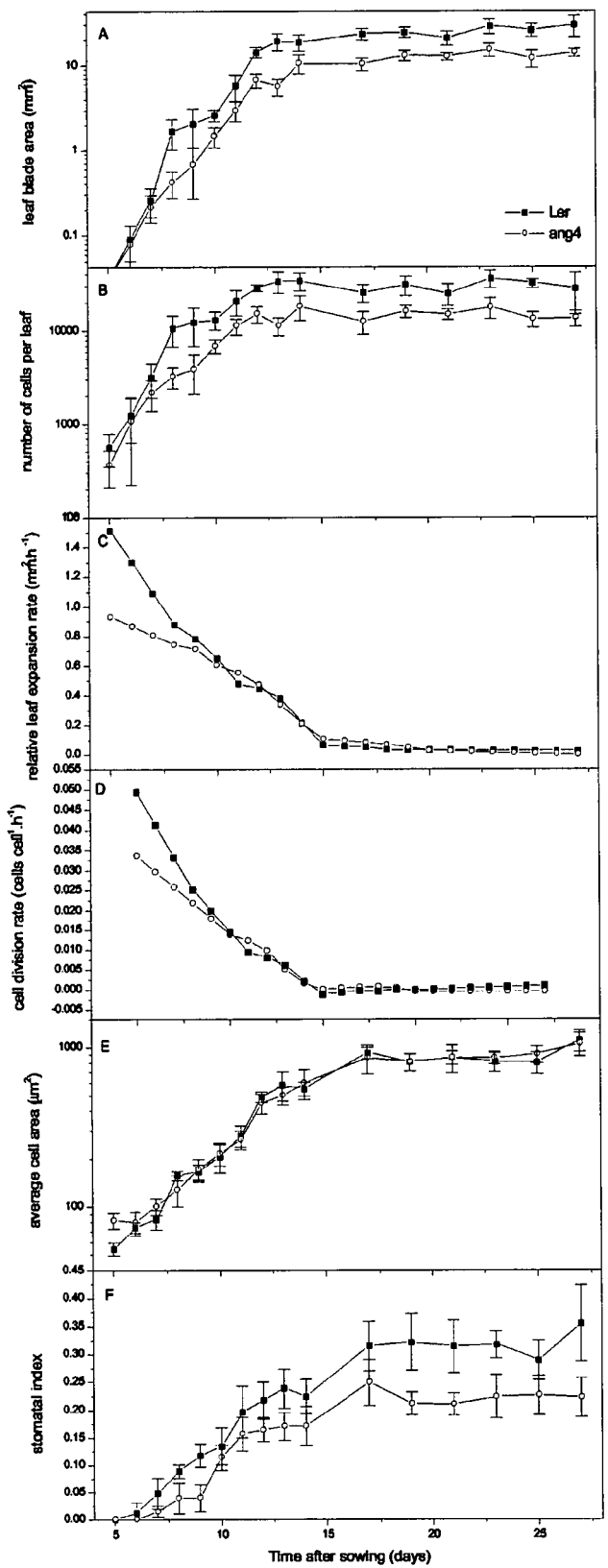
FIG. 13: Kinematic analysis of leaf growth of the first leaf pair of the wild-type Ler and the ang4-1 mutant. (A) leaf blade area, (B) epidermal cell number on the abaxial side of the leaf, (C) relative leaf expansion rate, (D) average cell division rates of the epidermal cells on the abaxial side of the leaf, (E) average epidermal cell size on the abaxial side of the leaf, (F) stomatal index on the abaxial side of the leaf. Error bars correspond to the standard deviation (n=5).

The effect of the ang4 mutation on leaf development and cell cycle duration was analyzed by a kinematic analysis on the first leaf pair of in vitro grown plants. Leaf blade area was similar in Ler and the ang4-1 mutant at the earliest observations. However, the increase in leaf area was slower in ang4-1 compared to Ler between 5 and 8 DAS (FIG. 13A). At maturity, the leaf blade area of ang4-1 was about 47% of those of Ler, with respectively 11 and 24 mm$^2$. During the same period, the number of cells per leaf also increased quicker in Ler than in ang4-1 (FIG. 13B). So, at maturity (after 18 DAS), the ang4-1 leaves contained only 48% the number of epidermal cells of Ler. Differences in the rate of increase of leaf area and cell number must be due to effects on cell expansion and division respectively. Indeed, between 5 and 10 DAS, the cell division rate and the relative leaf expansion rate (RLE) were lower in ang4-1 compared to Ler, but they decreased more slowly in the mutant (FIGS. 13 C and D). Consequently, the cell division rate and the RLE rate became similar in ang4-1 and Ler from the 10 DAS and along the expansion phase until no cell was dividing anymore at the 15 DAS. The expansion continued in both Ler and ang4-1 until the 18 DAS when the leaf reached the maturity. So, the ANG4 mutation alters the cell division and the leaf expansion only during the early stage of leaf development.

At this stage, the cells of ang4-1 were bigger than in Ler with an average cell area respectively of 82 μm$^2$ and 54 μm$^2$ at day 5 (FIG. 13E). After 7 DAS, no difference of the cell area could be observed at the later stages between ang4-1 and Ler showing that the balance between division and expansion rates is the same in ang4-1 and in Ler.

Because the final divisions give rise to stomata, the stomata index (SI) indicates the exit from cell cycle and the end of proliferation activity, which starts from the tip to the base of the leaf in *Arabidopsis* [De Veylder, 2001]. The SI also increased slower in ang4-1 compared to Ler between 5 and 8 DAS, resulting in the final Si in mature leaves being lower with 0.23 in average for ang4-1 and 0.35 for Ler (FIG. 13F). These data validate the previous data showing that the ANG4 mutation decreases the cell division activity at the early stage of leaf growth without modifying the duration of the proliferation and expansion phases. At 5 DAS, the average cell cycle duration, which is the inverse of cell division rate, was almost 50% longer in ang4-1 (20.6 h) than in Ler (14.1 h), and it was longer until 11 DAS where the cell cycle duration was the same in both genotypes (respectively 48.4 h and 50.7 h for Ler and ang4-1). To investigate deeper the effect of ang4 mutation on cell cycle progression, we analyzed wild-type and mutant leaves by means of flow cytometry. The ploidy level of the first leaf pair was determined throughout the development of wild-type and mutant leaves to reveal the changes in relative duration of G1/G2 phase during mitotic cell division and timing and amount of endoreduplication in the ang4-1 mutant.

Figure 14A:
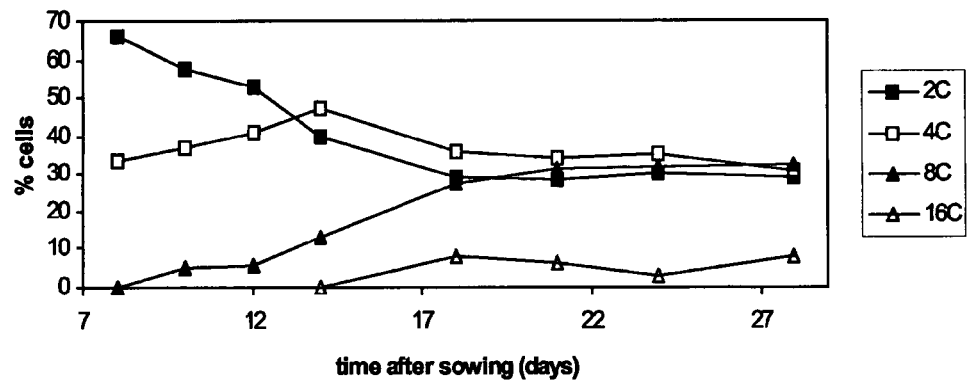
FIG. 14: Flow cytometry analysis of nuclear DNA content of the Ler (A) and ang4-1 mutant (B).
Figure 14B:
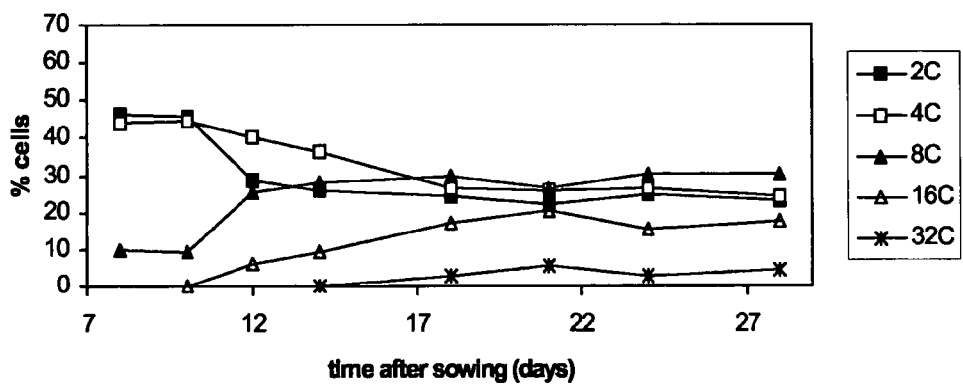

At 8 DAS when leaves could first be harvested, a shift is seen in the G1-to-G2 populations in the ang4-1 mutant compared to Ler (FIG. 14). In the mutant, the population of cells in 4C is similar to that in 2C (ang4-1; 2C=46.2%, 4C=44.0%), while in wild type, the number of cells in 4C is only half of those in 2C (Ler; 2C=66.2%, 4C=33.8%), suggesting that increased cell cycle duration is associated with a block at the G2-to-M transition point of the cell cycle in ang4-1. The exit from mitotis coincided with the start of the endocycles and could be seen by the increase of 4C content and the appearance of higher ploidy levels (8C, 16C). Cell cycle activity ended as evidenced by a stable DNA distribution around 18 DAS, coinciding with the end of growth. The endocycle was enhanced in the ang4-1 mutant from earliest stage with already 10% of the cells in 8C at 8 DAS, while this level of 8C was only reached at 13 DAS in Ler. The consequence was a higher ploidy levels in ang4-1. In the mature leaves, more than 4% of the cells contained a ploidy level of 32C in the ang4-1 mutant, while the ploidy level in mature Ler leaves only reached 16C. The exit from the endocycle occurred at the same date for both ang4-1 and Ler, at 18 DAS. So, when ANG4 is mutated, cells arrest in the G2/M phase of the cell cycle and proceed into endocycles instead. We postulate that the ANG4 protein has a function in the degradation of a cell cycle regulator(s) working at the G2-M transition of the cell cycle during early organ growth.

To confirm that these effects were not specific for the leaves, flow cytometry was done on roots, hypocotyls and first leaves at one time point in development (12 DAS). The ploidy levels obtained for the root and hypocotyls were comparable to those of the first leaves, indicating that ANG4 affects the cell cycle throughout plant development.

The flow cytometry profile of the ang1 allele, GABI_634H04, differs from that of the Col control and is similar but weaker to that of ang4: more endopolyploidy (presence of 32C), slight shift in the G1-to-G2 cell populations (reduced 2C cell number and increased 4C cell number). The mutational analysis of the ang1 allele indicates that ANGL (At1g55250) is also functional and might have functional redundancy with the ANG4 gene (At2g44950).

Example 9

ANG4 Overexpression Increases Leaf Size

Figure 15:
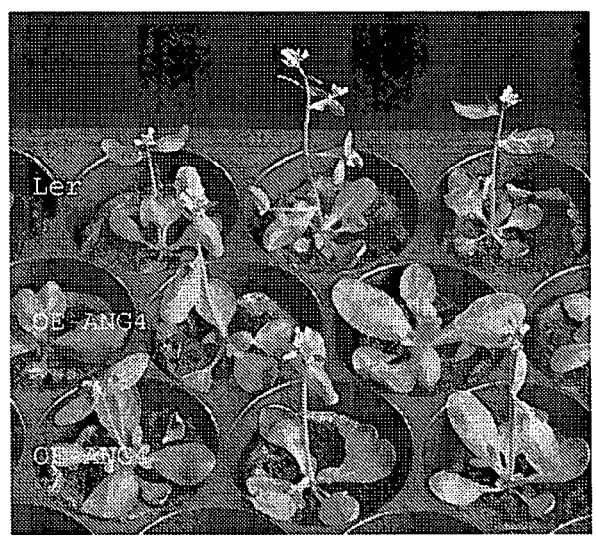
FIG. 15: Ler wild type and OE-ANG4 (T1) plants two weeks after transfer to soil.

Photographical observations of ANG4 overexpression plants (T1) clearly indicate that the plants have improved growth performance compared to wild type plants. For example, the rosette leaf size of the overexpression plants are considerably increased as can be seen in FIG. 15.

TABLE 1

Standard set of eight AFLP primer combinations used to detect linkage between 85 Col/Ler AFLP markers and ANG4 locus. Table obtained from Peters et al., 2004.

| Marker code | Selective nucleotide Sac1 + 1 | Selective nucleotide Sac1 + 2 | Selective nucleotide Mse1 + 1 | Selective nucleotide Mse1 + 2 | Number of AFLP markers |
|---|---|---|---|---|---|
| SM8 | A | A | C | T | 9 |
| SM57 | A | T | G | A | 13 |
| SM61 | A | T | T | A | 9 |
| SM205 | T | A | T | A | 12 |
| SM229 | T | G | C | A | 14 |
| SM233 | T | G | G | A | 10 |
| SM236 | T | G | G | T | 10 |
| SM240 | T | G | T | T | 8 |

TABLE 2

Genotypic scores of 9 recombinants using AFLP, InDel and SNP markers and L- indicates co-dominant marker, 1- dominant marker, 0- No marker H- heterozygous. Numbers in top row indicate the F3 individual recombinants. Recombinants indicated in blue was scored as ang4 mutants, green as wild type and turquoise as heterozygote.

| MARKER NAME | POSITION ON CONTINUOUS SEQ | PARENTS COL-0 | Ler | 227 | 635 | | 1472 | | | 1747 |
|---|---|---|---|---|---|---|---|---|---|---|
| CER458222 | 18657105 | C | L | H | C | H | H | H | H | C | L |
| CER442328 | 18519888 | C | L | H | C | C | H | H | | | |
| CER458219 | 18528422 | C | L | H | H | H | H | H | C | C | L |
| CER458218 | 18539154 | C | L | | C | H | H | H | H | C | C | |
| CER442324 | 18549847 | C | L | L | C | H | L | L | H | C | | H |
| CER442323 | 18559130 | C | L | L | C | H | L | L | H | C | C | H |
| CER458367 | 18565840 | C | L | L | C | H | L | L | L | C | C | H |
| CER442612 | | C | L | L | C | H | L | L | L | C | CH | H |
| SM33_202.4 | 18745473 | 1 | 0 | 0 | 1 | 1 | 0 | 0 | | | |
| CER458362 | 18753831 | C | L | L | H | H | L | L | L | C | H | H |

TABLE 3

Phenotypic scores of 9 recombinants: The scores were done at four time points over a period of 4 weeks both in soil and in vitro. In both growth conditions the scores were the same. Heterozygous indicates that the wild type and the mutants were observed while homozygous mutant implies only mutants were observed. Homozygous wild type indicates no mutant was observed in those recombinants.

| | F3 PROGENY | | | |
|---|---|---|---|---|
| ang4 RECOMBINANT LINE | NO. OF WILD TYPE | NO. OF MUTANTS | NEW PHENOTYPIC INTERPRETATION | PREVIOUS PHENOTYPIC INTERPRETATION |
| 227 | 0 | 66 | Homozygous mutant | Homozygous mutant |
| 387 | 53 | 0 | Homozygous wild type | Homozygous wild type |
| 635 | 52 | 0 | Homozygous wild type | Heterozygous |

TABLE 3-continued

Phenotypic scores of 9 recombinants: The scores were done at four time points over a period of 4 weeks both in soil and in vitro. In both growth conditions the scores were the same. Heterozygous indicates that the wild type and the mutants were observed while homozygous mutant implies only mutants were observed. Homozygous wild type indicates no mutant was observed in those recombinants.

| ang4 RECOMBINANT LINE | F3 PROGENY NO. OF WILD TYPE | NO. OF MUTANTS | NEW PHENOTYPIC INTERPRETATION | PREVIOUS PHENOTYPIC INTERPRETATION |
|---|---|---|---|---|
| 670 | 118 | 25 | Heterozygous | Homozygous mutant |
| 1389 | 28 | 5 | Heterozygous | Homozygous wild type |
| 1472 | 170 | 50 | Heterozygous | Heterozygous |
| 1607 | 53 | 0 | Homozygous wild type | Homozygous wild type |
| 1716 | 39 | 0 | Homozygous wild type | Homozygous wild type |
| 1747 | 63 | 18 | Heterozygous | Heterozygous |

TABLE 4

Recombinant used to delimit the ang4 mutation. Only 7 recombinants shown on the top row of the Table from recombinant 227 through recombinant 1747 were selected because they were the most informative recombinants while the other recombinants were ignored. The SNP markers and their position on continuous sequence are indicated indicates heterozygosity after a cross over event during meiosis. L- Ler, and C- Col ecotypes. The (?) in the Table means that the scoring of the recombinants was not clear.

| Marker Name | Position on Continuous Seq. | Col | Ler | F3 RECOMBINANTS | | | | | | |
|---|---|---|---|---|---|---|---|---|---|---|
| CER458222 | 18657105 | | | H | L | C | H | H | H | L |
| CER442328 | | | | H | L | C | | | | |
| CER458219 | 18670459 | C | L | H | H | H | H | C | H | L |
| CER458218 | 18681209 | C | L | | H | H | H | C | C | L |
| CER442324 | 18691819 | C | L | | H | H | H | C | ? | ? |
| CER442323 | | C | L | | | | H | C | CH | H |
| CER458367 | 18707856 | C | L | | | L | | | | |
| CER442612 | | C | L | | | L | | | | |
| SM33_202.4 | 18745473 | | | | | | | | | |
| CER458362 | 18753831 | | | | | L | C | C | H | |

Table 5. ANG4 candidate genes: The 4 candidate genes in the 27 kb region and their functions based on TAIR annotation. At—Arabidopsis thaliana, g—genomic.

| GENE CODE | FUNCTION |
|---|---|
| At2g44940 | Involved in DNA binding and transcription regulation by its AP2 domain |
| At2g44950 | It is a C3HC4 type zinc finger protein involved in zinc ion binding and as a E3ligase |
| At2g44970 | It is an expressed protein playing a role in lipid metabolism and catalytic activity |
| At2g44980 | Putative SNF2 transcription regulatory protein involved in ATP, DNA binding (Helicase activity) |

Table 6. Alleles for At2g44950 and At1g55250 genes: A, ANG4 alleles. Two SALK lines, SALK_122512 and SALK_044415 from SIGnAL collections and two GABI line, GABI_276D08, and GABI_306H08. B, alleles for the ANG4 homologues in Arabidopsis (At1g55250); SALK_071289 and SAKL_141948 from SIGnAL collections and GABI_634H04 and GABI_529603 from GABI collections.

A—At2g44950

| SALK LINES | GABI LINES | INSERTION SITE | POSITION IN CHROMOSOME 2 |
|---|---|---|---|
| SALK_122512 | | EXON 1 | 18549684 |
| SALK_044415 | | INTRON 3 | 18550469 |
| | GABI_306H08 | INTRON 2 | 18550191 |
| | GABI_276D08 | INTRON 13 | 18553269 |

B—At1g55250

| SALK LINES | GABI LINES | INSERTION SITE | POSITION ON CHROMOSOME 1 |
|---|---|---|---|
| SALK_071289 | | EXON 17 | 20615235 |
| SALK_141948 | | EXON 19 | 20615962 |
| | GABI_634H04 | EXON 13 | 20614348 |
| | GABI_529603 | INTRON19 | 20616201 |

TABLE 7

Differentially expressed genes in ang4 mutant compared to Ler and related to cell cycle and cytokinesis. Data were performed on microarrays ATH1 experiment with RNA from shoot apex of young plants grown in in vitro conditions. The p values are calculated according a Bayesian test of linear model and corrected by Holm's method.

| P. value | probes name | fold change expression | Sequence derived from | gene descriptions | process related |
|---|---|---|---|---|---|
| 1.29E−05 | 248413_at | 0.21 | At5g51600 | PLEIADE gene | cytokinesis |
| 5.78E−06 | 258098_at | 0.23 | At3g23670 | hypothetical protein similar to kinesin like protein | cytokinesis |
| 6.79E−06 | 248057_at | 0.26 | At5g55520 | putative myosin heavy chain protein | cytokinesis |
| 2.18E−06 | 261660_at | 0.26 | At1g18370 | HINKEL, kinesin heavy chain isolog | cytokinesis |
| 3.23E−06 | 264802_at | 0.26 | At1g08560 | KNOLLE, putative syntaxin-related protein | cytokinesis |
| 5.42E−07 | 261159_s_at | 0.28 | At1g34460 | putative cyclin | cell cycle |
| 2.89E−05 | 252691_at | 0.30 | At3g44050 | kinesin-like protein KLP2 protein | cytokinesis |
| 1.31E−04 | 257115_at | 0.30 | At3g20150 | kinesin-like protein | cytokinesis |
| 1.74E−06 | 247039_at | 0.31 | At5g67270 | putative microtubule-associated protein | cytokinesis |
| 2.97E−05 | 245607_at | 0.32 | At4g14330 | kinesin like protein | cytokinesis |
| 3.40E−06 | 255265_at | 0.32 | At4g05190 | kinesin like protein A | cytokinesis |
| 9.40E−05 | 253978_at | 0.32 | At4g26660 | putative kinesin | cytokinesis |
| 5.48E−05 | 263441_at | 0.33 | At2g28620 | putative kinesin-like spindle protein | cytokinesis |
| 1.12E−04 | 266009_at | 0.33 | At2g37420 | putative kinesin heavy chain | cytokinesis |
| 4.74E−05 | 261780_at | 0.36 | At1g76310 | CYCB2_4 (cyclin) | cell cycle |
| 2.53E−05 | 259151_at | 0.36 | At3g10310 | kinesin-like protein similar to carboxy-terminal kinesin 2 | cytokinesis |
| 8.84E−06 | 265349_at | 0.36 | At2g22610 | putative kinesin heavy chain | cytokinesis |
| 5.35E−06 | 257008_at | 0.38 | At3q14210 | Myrosinase-associated protein | cell cycle |
| 5.45E−04 | 253148_at | 0.38 | At4g35620 | CYCB2_2 (cyclin) | cell cycle |
| 2.41E−05 | 267618_at | 0.38 | At2g26760 | CYCB1_4 (cyclin) | cell cycle |
| 3.51E−05 | 254400_at | 0.40 | At4g21270 | kinesin-related protein katA | cytokinesis |
| 6.86E−05 | 245739_at | 0.40 | At1g44110 | CYCA1_1 (cyclin) | cell cycle |
| 1.80E−06 | 258573_at | 0.41 | At3g04260 | BC010 (E2Fb binding protein) | cell cycle |
| 2.96E−05 | 259851_at | 0.42 | At1g72250 | putative kinesin | cytokinesis |
| 1.53E−06 | 259978_at | 0.43 | At1g76540 | CDKB2_1 (Cyclin dependent kinase) | cell cycle |
| 2.71E−04 | 266401_s_at | 0.43 | At2g38620 | CDKB1_2 (Cyclin-dependent kinase) | cell cycle |
| 3.12E−04 | 262802_at | 0.45 | At1g20930 | CDKB2_2 (Cyclin-dependent kinase) | cell cycle |
| 2.30E−04 | 257267_at | 0.46 | At3g15030 | TCP family (E2Fa-DPa induced Transcription factor) | cell cycle |
| 1.69E−05 | 257524_at | 0.46 | At3g01330 | DEL3 (E2F-DP-like protein) | cell cycle |
| 3.53E−06 | 248150_at | 0.46 | At5g54670 | kinesin-like protein | cytokinesis |
| 3.35E−04 | 262081_at | 0.47 | At1g59540 | kinesin motor protein (kin2) | cytokinesis |
| 6.18E−05 | 245259_at | 0.47 | At4g14150 | kinesin like protein | cytokinesis |
| 2.72E−04 | 261605_at | 0.48 | At1g49580 | CDPK-related protein kinase | cell cycle |
| 1.59E−05 | 260329_at | 0.49 | At1g80370 | CYCA2_4 (cyclin) | cell cycle |
| 5.13E−05 | 263017_at | 0.49 | At2g17620 | CYCB2_1 (cyclin) | cell cycle |
| 4.54E−04 | 262752_at | 0.49 | At1g16330 | CYCB3_1 (cyclin) | cell cycle |
| 2.60E−05 | 266295_at | 0.49 | At2g29550 | tubulin beta-7 chain | cytokinesis |
| 3.78E−04 | 261765_at | 0.51 | At1g15570 | CYCA2_3 (cyclin) | cell cycle |
| 4.48E−04 | 252736_at | 0.52 | At3g43210 | TETRASPORE (TES), kinesin-like protein ZCF125 | cytokinesis |
| 7.37E−04 | 262494_at | 0.54 | At1g21810 | myosin-like protein | cytokinesis |
| 8.43E−04 | 265464_at | 0.54 | At2g37080 | putative myosin heavy chain | cytokinesis |
| 7.93E−04 | 250386_at | 0.55 | At5g11510 | MYB3R4 (transcription factor) | cell cycle |
| 1.06E−03 | 264061_at | 0.55 | At2g27970 | CKS2 (CDK binding protein) | cell cycle |
| 1.06E−03 | 246683_at | 0.56 | At5g33300 | putative protein chromokinesin KIF4 | cytokinesis |
| 8.76E−03 | 250685_at | 0.56 | At5g06670 | kinesin heavy chain-like protein | cytokinesis |
| 8.23E−04 | 261639_at | 0.57 | At1g50010 | putative tubulin alpha-2/alpha-4 chain | cytokinesis |
| 3.16E−03 | 245576_at | 0.57 | At4g14770 | CPP1-related transcription factor family (E2Fa-DPa induced TF). | cell cycle |
| 4.07E−03 | 249095_at | 1.44 | At5g43900 | myosin heavy chain MYA2 | cytokinesis |
| 1.08E−03 | 251052_at | 1.54 | At5g02470 | DPA transcription factor | cell cycle |
| 1.45E−04 | 250923_at | 1.69 | At5g03455 | GTPV2 (putative CDC25 homolog) | cell cycle |
| 4.59E−04 | 260765_at | 1.79 | At1g49240 | actin 8 | cytokinesis |
| 2.13E−04 | 250844_at | 1.97 | At5g04470 | SIAMESE gene (SIM) | cell cycle |
| 4.89E−03 | 264006_at | 2.02 | At2g42430 | homeodomain (ATHB-6) (E2Fa-DPa induced TF) | cell cycle |
| 1.93E−06 | 253217_at | 2.58 | At4g34970 | actin depolymerizing factor-like protein | cytokinesis |
| 1.17E−03 | 250666_at | 3.25 | At5g07100 | WRKY family (E2Fa-DPa induced Transcription factor) | cell cycle |
| 1.65E−09 | 253890_s_at | 3.84 | At5g54100 | Putative protein contains similarity to stomatin like protein | cell cycle |

TABLE 8

Differentially expressed genes in ang4 mutant compared to Ler and related to plant development. Data were performed on microarrays ATH1 experiment with RNA from shoot apex of young plants grown in in vitro conditions. The p values are calculated according a Bayesian test of linear model and corrected by Holm's method.

| P. value | probes name | fold change expression | Sequence derived from | gene descriptions | |
|---|---|---|---|---|---|
| 3.28E−06 | 259686_at | 0.26 | At1g63100 | transcription factor SCARECROW | development |
| 2.15E−03 | 257221_at | 0.46 | At3g27920 | GLABRA1 (GL1), MYB family transcription factor | development |
| 1.26E−05 | 265454_at | 0.50 | At2g46530 | putative ARF1 family auxin responsive transcription factor | development |
| 1.86E−03 | 263013_at | 1.92 | At1g23380 | KNAT6, knotted-like homeobox protein | development |
| 9.50E−05 | 260334_at | 1.96 | At1g70510 | KNAT2, homeotic protein (ATK1) | development |
| 7.91E−04 | 263194_at | 2.58 | At1g36060 | AP2 domain transcription factor | development |
| 5.10E−07 | 259680_at | 2.86 | At1g77690 | putative AUX1-like permease | development |
| 3.21E−08 | 265813_at | 3.47 | At2g18060 | putative NAM (no apical meristem)-like protein | development |
| 3.23E−10 | 245173_at | 8.79 | At2g47520 | putative AP2 domain transcription factor, aintegumenta-like protein | development |

TABLE 9

Primers used for ANG4 candidate genes amplification and sequencing

| GENE NAME | PRIMER DIRECTION | MIPS POSITION | PRIMER SEQUENCE | FRAGMENT SIZE | SEQ ID NO: |
|---|---|---|---|---|---|
| At2g44940 | F | 67 | TGTT AAGAGGTGAC GCACATG | 943 | 9 |
|  | R | 1010 | CGGCGGCTTGAATGTCTTTA |  | 10 |
| At2g44940 | F | 800 | T AGAGGAGTGA GGATGAGGAG TT | 723 | 11 |
|  | R | 1523 | GCTAGGAAAAAAAAAGAAATTGT |  | 12 |
| At2g44960 | F | 166 | TTTTT GTTTCTGTGAGTGCTGTG | 1119 | 13 |
|  | R | 1285 | TCTCAGTAGCACCAGTTTCAAG |  | 14 |
| At2g44960 | F | 625 | CTTCT TCATCTCCCC CTTGTGC | 1327 | 15 |
|  | R | 1952 | ATAAATACACAGGCGTGGAATTGG |  | 16 |
| At2g44970 | F | 86 | TATGT GTCGCCCGTC TTCTTTCTT | 854 | 17 |
|  | R | 940 | ATGCCAATGAACAACAAGTAAAGA |  | 18 |
| At2g44970 | F | 800 | TTCCTAATGT TGTTTGCCGTTTCA | 827 | 19 |
|  | R | 1627 | CATGGGGGTGGAAATAGTATCCT |  | 20 |
| At2g44970 | F | 1468 | TAC TCAGTATGCA ATTCCACGTT CATAT | 1114 | 21 |
|  | R | 2582 | TCTCTCTCGCATTTTTCTCAACCG |  | 22 |
| At2g44970 | F | 2443 | AACGAAAT TCTCAAAGATGGGTTT | 1238 | 23 |
|  | R | 3681 | AACGAAATTCTCAAAGATGGGTTT |  | 24 |
| At2g44980 | F | 73 | CGTCACAC CATCCACACC ACTTG | 1120 | 25 |
|  | R | 1193 | GACGGCAATACTTATCGCCAACATAT |  | 26 |
| At2g44980 | F | 927 | AATT GGACCAGATG GGATTGGGAA AG | 1032 | 27 |
|  | R | 1959 | TCCACACAAAAATGTCAGAGTGCTTAGC |  | 28 |
| At2g44980 | F | 1799 | CTTGATTACTGG CACACCTATC CA | 943 | 29 |
|  | R | 2742 | GGGAAAAGAGGAGGACACGATG |  | 30 |
| At2g44980 | F | 2480 | T GTTTATCTCC CTATCTATTT CCTTG | 927 | 31 |
|  | R | 3404 | CTTTCTCTCTGCCCTCCTCAA |  | 32 |
| At2g44980 | F | 3122 | TGGAATACA TCGGCATAGA GAAAG | 1053 | 33 |
|  | R | 4175 | TAAACTCGGATGCTCGGTGATAAG |  | 34 |
| At2g44980 | F | 3836 | CCAGGAAAAGGCA GAAGAGAAGA | 980 | 35 |
|  | R | 4816 | CATTGTGTGATTCAGGGAGATCGA |  | 36 |
| At2g44950 | F | 11 | GGGCGTTTTTCCCAGTGTTG | 1014 | 37 |
|  | R | 1005 | TCAGCCCGCAGAGAATGAAT |  | 38 |
| At2g44950 | F | 845 | TCCCACCCACACCTGTTTCA | 1182 | 39 |
|  | R | 2007 | TTCCGCAGCAGCCAACATTT |  | 40 |

TABLE 9-continued

Primers used for ANG4 candidate genes amplification and sequencing

| GENE NAME | PRIMER DIRECTION | MIPS POSITION | PRIMER SEQUENCE | FRAGMENT SIZE | SEQ ID NO: |
|---|---|---|---|---|---|
| At2g44950 | F | 1886 | GAAGCCAAGGAACAGGAGTA | 947 | 41 |
|  | R | 2813 | CATACGGGCACACACAGATA |  | 42 |
| At2g44950 | F | 2652 | CTCGCCCATTGTTGTTTCAG | 1241 | 43 |
|  | R | 3873 | AATTGCGGAAACCATGTTCC |  | 44 |
| At2g44950 | F | 3065 | TGGGGCATTAGAACTGGAAC | 1010 | 45 |
|  | R | 4055 | TCCCAAGGATCGAAGTCTTT |  | 46 |

REFERENCES

Anami, S. (2004). Cloning and functional analysis of genes controlling organ growth and development in *Arabidopsis thaliana*. Masters thesis for International Post-graduate course on Molecular Biology (VUB, Brussels).

Autran D, Jonak C, Belcram K, Beemster G T S, Kronenberger J. Grandjean O. Inzé D, Traas J. 2002. Cell numbers and leaf development in *Arabidopsis*: a functional analysis of the STRUWWELPETER gene. *The EMBO Journal* 21, 6036-6049.

Berna, G., Robles, P and Micol, J. L. (1999) A mutational analysis of leaf morphogenesis in *Arabidopsis thaliana*. Genetics, 152, 729-742

De Veylder L, Joubes J. Inze D. (2003) Plant cell cycle transitions. *Curr Opin Plant Biol.*, 6, 536-543.

Cnops G. Jover-Gil S. Peters J. Neyt P. De Block S. Robles P. Ponce M, Gerats T. Micol J. Van Lijsebettens M (2004) The rotunda2 mutants identify a role for the LEUNIG gene in vegetative leaf morphogenesis. Journal of Experimental Botany 55: 1529-1539

De Veyider L, Beeckman T. Beemster G T S, Krols L, Terras F. Landrieu I, Van Der Schueren E, Maes S, Naudts M, Inzé D (2001) Functional analysis of cyclin-dependent kinase inhibitors of *Arabidopsis*. Plant Cell 13: 1653-1667

Erickson R O (1976) Modeling of plant growth. Annu. Rev. Plant Physiol. 27: 407-434

Galbraight D W, Harkins K R, Knapp S (1991) Systemic endopolyploidy in *Arabidopsis thaliana*. Plant Physiol. 96: 985-989

Hightower, R. C. and Meagher, R. B. (1986). The molecular evolution of actin. Genetics 114, 315-332.

Kamiya N. Itoh J. Morikami A, Nagato Y. Matsuoka M. 2003. The SCARECROW gene's role in asymmetric cell divisions in rice plants. *Plant J.* 36, 45-54.

Karimi, M., Inzé, D. And Depicker, A. (2002). GATEWAY vectors for *Agrobacterium*-mediated plant transformation. Trends in Plant Sciences 7, 193-195.

Liscum E, Reed J W. 2002. Genetics of Aux/IAA and ARF action in plant growth and development. *Plant Mol Biol*, 49, 387-400.

Lonnstedt I, Speed T 2002. Replicated microarray data. Statistica Sinica 12, 31-46.

Muller S. Fuchs E, Ovecka M, Wysocka-Diller J. Benfey P N, Hauser M T. 2002. Two new loci, PLEIADE and HYADE, implicate organ-specific regulation of cytokinesis in *Arabidopsis. Plant Physiol.*, 130, 312-324.

Muller I, Wagner W. Volker A, Schellmann S, Nacry P. Kuttner F. Schwarz-Sommer Z. Mayer U. Jurgens G. 2003. Syntaxin specificity of cytokinesis in *Arabidopsis. Nat Cell Biol.*, 5, 531-534.

Nelissen H. Clarke J H, De Block M, De Block S. Vanderhaeghen R. Zielinski R E, Dyer T. Lust S. Inzé D, Van Lijsebettens M. 2003. DRL1, a homolog of the yeast TOT4/KTI12 protein, has a function in meristem activity and organ growth in plants. *The Plant Cell* 15, 639-654.

Peters J L, Cnops G. Neyt P. Zethof J. Cornelis K, Van Lijsebettens M, Gerats T. 2004. An AFLP-based genome-wide mapping strategy: a practical approach to positional cloning. *Theoretical and Applied Genetics* 108, 321-327.

Pyke K A, Marrison J L, Leech R M. 1991. Temporal and spatial development of the cells of the expanding first leaf of *Arabidopsis thaliana* (L.) Heynh. *Journal of Expermental Botany* 42, 1407-1416.

Reddy A S, Day I S. 2001. Kinesins in the *Arabidopsis* genome: a comparative analysis among eukaryotes. *BMC Genomics*. 2, Epub 25.

Robles, P. and Micol, J. L. (2001). Genome-wide linkage analysis of *Arabidopsis* genes required for leaf development. Mol. Genet. Genomics. 266, 12-19.

Schiefelbein J. 2003. Cell-fate specification in the epidermis: a common patterning mechanism in the root and shoot. *Curr Opin Plant Biol.*, 6, 74-78.

Smyth G K, Yang Y H, Speed T 2003. Statistical issues in cDNA microarray data analysis. Meth. Mol. Biol. 224, 111-136.

Stone S. Hauksdóttir H. Herschleb J. Kraft E, Callis J (2005) Functional analysis of the RING-type ubiquitin ligase family of *Arabidopsis*. Plant Physiol. 137: 13-30.

Strompen G. El Kasmi F. Richter S. Lukowitz W. Assaad F F, Jurgens G. Mayer U. 2002. The *Arabidopsis* HINKEL gene encodes a kinesin-related protein involved in cytokinesis and is expressed in a cell cycle-dependent manner. *Curr Biol.*, 12, 153-158.

Traas J. Vernoux T. 2002. The shoot apical meristem: the dynamics of a stable structure. *Philos Trans R Soc Lond B Biol Sci.*, 357, 737-747.

Tsiantis M, Hay A. 2003. Comparative plant development: the time of the leaf? *Nat Rev Genet*, 4, 169-180.

Tsuge T. Tsukaya H. Uchimiya H.1996. Two independent and polarized processes of cell elongation regulate leaf blade expansion in *Arabidopsis thaliana* (L.) Heynh. *Development* 122, 1589-1600.

Van Lijsebettens M, Clarke J. 1998. Leaf development in *Arabidopsis*. *Plant Physiology and Biochemistry* 36, 47-60.

Wu Z. Irizarry K A 2004. Preprocessing of oligonucleotide array data. Nat. Biotechnol. 22, 656-658.

Yang C Y, Spielman M, Coles J P, Li Y. Ghelani S. Bourdon V, Brown R C, Lemmon B E, Scott R J, Dickinson H G. 2003. TETRASPORE encodes a kinesin required for male meiotic cytokinesis in *Arabidopsis*. *Plant J.,* 34, 229-240.

---

The invention claimed is:

1. A method of modulating cell number in a plant organ or part thereof, said method comprising:
   transforming the plant organ or part thereof with an isolated nucleic acid molecule encoding a protein comprising SEQ ID NO:2, wherein the nucleic acid molecule is operably lined to a promoter.

2. The method according to claim 1, wherein said plant organ is a plant leaf or a plant root.

3. The method according to claim 1, wherein said plant organ comprises a leaf palisade cell.

4. The method according to claim 1, so as to modulate leaf morphology.

5. A method of increasing plant biomass, said method comprising:
   transforming the plant with an isolated nucleic acid molecule encoding a protein comprising SEQ ID NO:2, wherein the nucleic acid molecule is operably lined to a promoter.

6. The method according to claim 2, wherein said plant organ comprises a leaf palisade cell.

7. The method according to claim 2, so as to modulate leaf morphology.

8. The method according to claim 6, so as to modulate leaf morphology.

9. The method according to claim 1, wherein the protein consists of SEQ ID NO:2.

10. The method according to claim 5, wherein the protein consists of SEQ ID NO:2.

11. The method according to claim 1, wherein the gene is overexpressed.

12. The method according to claim 5, wherein the gene is overexpressed.

* * * * *

SEQUENCE LISTING

<160> NUMBER OF SEQ ID NOS: 54

<210> SEQ ID NO 1
<211> LENGTH: 3289
<212> TYPE: DNA
<213> ORGANISM: Arabidopsis thaliana
<220> FEATURE:
<221> NAME/KEY: misc_feature
<223> OTHER INFORMATION: genbank NM_130060

<400> SEQUENCE: 1

```
tcactcttgt ttttgtttct gtgagtgctg tgtgtgttct cggtttgtaa tatctaagtc      60
gcacaaagat cagacaaagt ctgtttgcgt ttgatagcat tagagtctga tcgaatttgg     120
aagacctgtg agattagggt ttcttttgt ttgttttttt ttattccgaa ggagagctgc     180
ggagcaattg gaattacctc ggttaaagca atcacgtagc tttggatcgt ttagggtttt     240
ctcattgggt ttggggggatt tgtattcgag cttcctcaaa ctcaatctga tggtgatgtg     300
agacaaggct taatcctgtt aattggcgat tctagggttt ttcaatggcg agcacaggcg     360
agcctgaccg taaaaggcgt cactttagct ccatatcacc ttctgaagct gcagccgccg     420
taaagaaaca gcctttcttt tggccctcct ccgaggacaa gcttgatact gcagttcttc     480
agttccaaaa tcttaagcta tcacaaaagc tagaggctca gcaggttgag tgttctattc     540
ttgaggataa actctctcag atcaaggaaa aacaattacc atacaactcc agtttgaaga     600
ctgtccataa gtcttgggaa aagcttacag cttcagtgga atcatgctct gttcgtgtga     660
gtgattcaag cagcggagct cataggtttg taaacaagga ggatgggtct tctccagccg     720
tgaaaaacga tttcatcaac cggctacttg aaactggtgc tactgagagc tcctcatcca     780
atatctgctc gaatcagatg gaagaaaatg gagtgaatac gtcaagccag atgacgcaaa     840
ccttgtataa tctagtagcc gcgacagagg atttgaggtg tctgaaggat gaattatatc     900
ccacagttct cagaaccaat cttggtaaag atttgtgcgg tcagctagct ctgagtgagt     960
tggaatcaga aattaaaagt ttcagagggg atctagatga tgtacttgtg aagttcaaat    1020
cactttctag agaattgcag agtcatcgcg atgctgatgc taaagttaga gtagacctca    1080
aacgaataag aggggagcta gaggatgagg ttgtggagct tcagcagtgt aatggtgact    1140
tgtcagcatt gagagcagaa agggatgcaa cagctgggc gttttttccca gtgttgagtc    1200 ttggaaataa gcttgctacc agtgatcggg agagggataa acaaagggat ctgcaagaca    1260
tggaaacagt tctgaaagag ttaacggtcc tggcttcagg caggctacaa cagctaaaaa    1320
atcttcatga ggagaggaca aagatgcttg gaaaaatgag taatttacag aacaagtcaa    1380
agtctgtgag gtgcatctca tcttctcaag cctgcctttc tttgaaagac cagctagaaa    1440
aatccaaaga agcagttttc cagtatatgg ctttacttga gaaactgcag gttgaaaaag    1500
atagtatagt ctggaaggaa agggagataa atataaaaaa tgaactaggt gatgtttctc    1560
gaaagacgtc tgctgttact gattctagaa tggcttcttt ggattcggag atacagaaac    1620
```

```
aactggatga aaaaatgcga atcaagacta ggctgggaaa tatatcaaga gagcgaggta    1680
gaaaagaaat ctttgcagat atgaaggcat taatttcttc gttccccgag gaaatgagtt    1740
ccatgcgtag tcaattaaac aattataaag agactgctgg aggtattcat tctctgcggg    1800
ctgatgtcca gtccctctct ggggttctat gtaggaagac aaaagagtat gaagcattgc    1860
aattgagatc agctgattat gcttctcagt taggtgacct gaatgctacg gtttgtgatt    1920
tgaagaacag tcatgaggag ttaaagttgt ttctggacat gtataaacgt gagtccactg    1980
atgcgaggga catagctgaa gccaaggaac aggagtacag gcttgggct catgttcaga     2040 gtttgaaatc atcccttgat gagcaaaatc tggagttgcg cgttaaggca gcaaatgaag    2100
ctgaagccgt tcccaacaa atgttggctg ctgcggaagc agagattgct gatttaaggc     2160
agaaaatgga tgattgtaaa agggatgtcg ccaagcattc tgatatcttg aaatctaaac    2220
atgaagaaca tggaacatat ctttctgaaa tacagacaat tggaagtgcc tatgaggaca    2280
ttgtaccgca aaaccaacag cttttgcttc aagttacaga gagggatgac tataacatca    2340
agcttttctt ggaaggcata acttctaggc agatgcaaga tactctgctt atcgataaat    2400
acatcatgga taaggatata cagcaaggca gtgcatatgc cagtttccta tccaagaaat    2460
catcaagaat tgaagatcag ttgaggttct gcacagatca gtttcagaaa ctagcggaag    2520
ataaatatca aaagtctgtt tctcttgaaa atctgcaaaa gaaacgtgca gacatcggga    2580
atggcttgga acaagctagg tcaaggctgg aggagtccca ttctaaagtt gagcaaagtc    2640
ggctggatta tggggcatta gaactggaac tggagattga aaggttcaat aggagaagga    2700
tagaggagga aatggaaata gccaaaaaga aagtttctcg tcttcggtct ctcatagaag    2760
gatcatcggc cattcaaaag ctccgacaag aactcagtga atttaaagaa attctgaagt    2820
gtaaggcctg caacgatcgc ccaaaagagg tggtgattac gaagtgctac catttgttct    2880
gcaacccatg tgtgcaaaag ctcacaggaa ctcgacaaaa gaagtgtcca acatgctcag    2940
caagttttgg accaaatgat attaaaccta tctacatatg accgcaccaa acactctga     3000 gcatgatgat gtatgatgaa actgtgaaac acacacaggt acttttctc atataggata     3060 aacattagat ctctctgtaa ttattactct cttttattgg gaaaggtcat gaagaataat    3120
tggatatggc aaatcagagt ttttgaggaa ccatttggg attttgataa tgtgatagag     3180
aataggtaac actgttaggg tttatgtctt tggtgatact tcctttttgt ttgtaatttg    3240
gaacatggtt tccgcaattg attttcaat taaatcttct tttttgttc                3289
```

<210> SEQ ID NO 2
<211> LENGTH: 878
<212> TYPE: PRT
<213> ORGANISM: Arabidopsis thaliana
<220> FEATURE:
<221> NAME/KEY: MISC_FEATURE
<222> LOCATION: (826)..(864)
<223> OTHER INFORMATION: RING finger motif

<400> SEQUENCE: 2

Met Ala Ser Thr Gly Glu Pro Asp Arg Lys Arg His Phe Ser Ser
1               5                   10                  15

Ile Ser Pro Ser Glu Ala Ala Ala Val Lys Lys Gln Pro Phe Phe
                20                  25                  30

Trp Pro Ser Ser Glu Asp Lys Leu Asp Thr Ala Val Leu Gln Phe Gln
            35                  40                  45

Asn Leu Lys Leu Ser Gln Lys Leu Glu Ala Gln Gln Val Glu Cys Ser
        50                  55                  60

```
Ile Leu Glu Asp Lys Leu Ser Gln Ile Lys Glu Lys Gln Leu Pro Tyr
 65                  70                  75                  80

Asn Ser Ser Leu Lys Thr Val His Lys Ser Trp Glu Lys Leu Thr Ala
                 85                  90                  95

Ser Val Glu Ser Cys Ser Val Arg Val Ser Asp Ser Ser Ser Gly Ala
            100                 105                 110

His Arg Phe Val Asn Lys Glu Asp Gly Ser Ser Pro Ala Val Lys Asn
        115                 120                 125

Asp Phe Ile Asn Arg Leu Leu Glu Thr Gly Ala Thr Glu Ser Ser Ser
    130                 135                 140

Ser Asn Ile Cys Ser Asn Gln Met Glu Glu Asn Gly Val Asn Thr Ser
145                 150                 155                 160

Ser Gln Met Thr Gln Thr Leu Tyr Asn Leu Val Ala Ala Thr Glu Asp
                165                 170                 175

Leu Arg Cys Leu Lys Asp Glu Leu Tyr Pro Thr Val Leu Arg Thr Asn
            180                 185                 190

Leu Gly Lys Asp Leu Cys Gly Gln Leu Ala Leu Ser Glu Leu Glu Ser
        195                 200                 205

Glu Ile Lys Ser Phe Arg Gly Asp Leu Asp Asp Val Leu Val Lys Phe
    210                 215                 220

Lys Ser Leu Ser Arg Glu Leu Gln Ser His Arg Asp Ala Asp Ala Lys
225                 230                 235                 240

Val Arg Val Asp Leu Lys Arg Ile Arg Gly Glu Leu Glu Asp Glu Val
                245                 250                 255

Val Glu Leu Gln Gln Cys Asn Gly Asp Leu Ser Ala Leu Arg Ala Glu
            260                 265                 270

Arg Asp Ala Thr Ala Gly Ala Phe Phe Pro Val Leu Ser Leu Gly Asn
        275                 280                 285

Lys Leu Ala Thr Ser Asp Arg Glu Arg Asp Lys Gln Arg Asp Leu Gln
    290                 295                 300

Asp Met Glu Thr Val Leu Lys Glu Leu Thr Val Leu Ala Ser Gly Arg
305                 310                 315                 320

Leu Gln Gln Leu Lys Asn Leu His Glu Glu Arg Thr Lys Met Leu Gly
                325                 330                 335

Lys Met Ser Asn Leu Gln Asn Lys Ser Lys Ser Val Arg Cys Ile Ser
            340                 345                 350

Ser Ser Gln Ala Cys Leu Ser Leu Lys Asp Gln Leu Glu Lys Ser Lys
        355                 360                 365

Glu Ala Val Phe Gln Tyr Met Ala Leu Leu Glu Lys Leu Gln Val Glu
    370                 375                 380

Lys Asp Ser Ile Val Trp Lys Glu Arg Glu Ile Asn Ile Lys Asn Glu
385                 390                 395                 400

Leu Gly Asp Val Ser Arg Lys Thr Ser Ala Val Thr Asp Ser Arg Met
                405                 410                 415

Ala Ser Leu Asp Ser Glu Ile Gln Lys Gln Leu Asp Glu Lys Met Arg
            420                 425                 430

Ile Lys Thr Arg Leu Gly Asn Ile Ser Arg Glu Arg Gly Arg Lys Glu
        435                 440                 445

Ile Phe Ala Asp Met Lys Ala Leu Ile Ser Ser Phe Pro Glu Glu Met
    450                 455                 460

Ser Ser Met Arg Ser Gln Leu Asn Asn Tyr Lys Glu Thr Ala Gly Gly
465                 470                 475                 480
```

```
Ile His Ser Leu Arg Ala Asp Val Gln Ser Leu Ser Gly Val Leu Cys
            485                 490                 495

Arg Lys Thr Lys Glu Tyr Glu Ala Leu Gln Leu Arg Ser Ala Asp Tyr
            500                 505                 510

Ala Ser Gln Leu Gly Asp Leu Asn Ala Thr Val Cys Asp Leu Lys Asn
            515                 520                 525

Ser His Glu Glu Leu Lys Leu Phe Leu Asp Met Tyr Lys Arg Glu Ser
            530                 535                 540

Thr Asp Ala Arg Asp Ile Ala Glu Ala Lys Glu Gln Glu Tyr Arg Ala
545                 550                 555                 560

Trp Ala His Val Gln Ser Leu Lys Ser Ser Leu Asp Glu Gln Asn Leu
                565                 570                 575

Glu Leu Arg Val Lys Ala Ala Asn Glu Ala Glu Ala Val Ser Gln Gln
            580                 585                 590

Met Leu Ala Ala Ala Glu Ala Glu Ile Ala Asp Leu Arg Gln Lys Met
            595                 600                 605

Asp Asp Cys Lys Arg Asp Val Ala Lys His Ser Asp Ile Leu Lys Ser
610                 615                 620

Lys His Glu Glu His Gly Thr Tyr Leu Ser Glu Ile Gln Thr Ile Gly
625                 630                 635                 640

Ser Ala Tyr Glu Asp Ile Val Pro Gln Asn Gln Gln Leu Leu Leu Gln
                645                 650                 655

Val Thr Glu Arg Asp Asp Tyr Asn Ile Lys Leu Phe Leu Glu Gly Ile
            660                 665                 670

Thr Ser Arg Gln Met Gln Asp Thr Leu Leu Ile Asp Lys Tyr Ile Met
            675                 680                 685

Asp Lys Asp Ile Gln Gln Gly Ser Ala Tyr Ala Ser Phe Leu Ser Lys
            690                 695                 700

Lys Ser Ser Arg Ile Glu Asp Gln Leu Arg Phe Cys Thr Asp Gln Phe
705                 710                 715                 720

Gln Lys Leu Ala Glu Asp Lys Tyr Gln Lys Ser Val Ser Leu Glu Asn
                725                 730                 735

Leu Gln Lys Lys Arg Ala Asp Ile Gly Asn Gly Leu Glu Gln Ala Arg
            740                 745                 750

Ser Arg Leu Glu Glu Ser His Ser Lys Val Glu Gln Ser Arg Leu Asp
            755                 760                 765

Tyr Gly Ala Leu Glu Leu Glu Leu Glu Ile Glu Arg Phe Asn Arg Arg
            770                 775                 780

Arg Ile Glu Glu Glu Met Glu Ile Ala Lys Lys Lys Val Ser Arg Leu
785                 790                 795                 800

Arg Ser Leu Ile Glu Gly Ser Ser Ala Ile Gln Lys Leu Arg Gln Glu
                805                 810                 815

Leu Ser Glu Phe Lys Glu Ile Leu Lys Cys Lys Ala Cys Asn Asp Arg
            820                 825                 830

Pro Lys Glu Val Val Ile Thr Lys Cys Tyr His Leu Phe Cys Asn Pro
            835                 840                 845

Cys Val Gln Lys Leu Thr Gly Thr Arg Gln Lys Lys Cys Pro Thr Cys
            850                 855                 860

Ser Ala Ser Phe Gly Pro Asn Asp Ile Lys Pro Ile Tyr Ile
865                 870                 875

<210> SEQ ID NO 3
<211> LENGTH: 20
<212> TYPE: DNA
```

```
<213> ORGANISM: Artificial Sequence
<220> FEATURE:
<223> OTHER INFORMATION: primer

<400> SEQUENCE: 3
ctcgcccatt gttgtttcag                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aattgcggaa accatgttcc                                              20

<210> SEQ ID NO 5
<211> LENGTH: 20
<212> TYPE: DNA
<213> ORGANISM: Artificial Sequence
<220> FEATURE:
<223> OTHER INFORMATION: primer Defle44

<400> SEQUENCE: 5
tgctggacgt gaccttactg                                              20

<210> SEQ ID NO 6
<211> LENGTH: 20
<212> TYPE: DNA
<213> ORGANISM: Artificial Sequence
<220> FEATURE:
<223> OTHER INFORMATION: primer Defle45

<400> SEQUENCE: 6
gggctggaac aagacttctg                                              20

<210> SEQ ID NO 7
<211> LENGTH: 20
<212> TYPE: DNA
<213> ORGANISM: Artificial Sequence
<220> FEATURE:
<223> OTHER INFORMATION: primer syana_01

<400> SEQUENCE: 7
tgctcgaatc agatggaaga                                              20

<210> SEQ ID NO 8
<211> LENGTH: 20
<212> TYPE: DNA
<213> ORGANISM: Artificial Sequence
<220> FEATURE:
<223> OTHER INFORMATION: primer syana_02

<400> SEQUENCE: 8
agctagctga ccgcacaaat                                              20

<210> SEQ ID NO 9
<211> LENGTH: 21
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 9
```
tgttaagagg tgacgcacat g                                              21

<210> SEQ ID NO 10
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 10
cggcggcttg aatgtcttta                                                20

<210> SEQ ID NO 11
<211> LENGTH: 23
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 11
tagaggagtg aggatgagga gtt                                            23

<210> SEQ ID NO 12
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 12
gctaggaaaa aaaaagaaa ttgt                                            24

<210> SEQ ID NO 13
<211> LENGTH: 23
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 13
tttttgtttc tgtgagtgct gtg                                            23

<210> SEQ ID NO 14
<211> LENGTH: 22
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 14
tctcagtagc accagtttca ag                                             22

<210> SEQ ID NO 15
<211> LENGTH: 22
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 15
cttcttcatc tcccccttgt gc                                             22

```
<210> SEQ ID NO 16
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 16
ataaatacac aggcgtggaa ttgg                                              24

<210> SEQ ID NO 17
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 17
tatgtgtcgc ccgtcttctt tctt                                              24

<210> SEQ ID NO 18
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 18
atgccaatga acaacaagta aaga                                              24

<210> SEQ ID NO 19
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 19
ttcctaatgt tgtttgccgt ttca                                              24

<210> SEQ ID NO 20
<211> LENGTH: 23
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 20
catgggggtg gaaatagtat cct                                               23

<210> SEQ ID NO 21
<211> LENGTH: 28
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 21
tactcagtat gcaattccac gttcatat                                          28
```

```
<210> SEQ ID NO 22
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 22
tctctctcgc atttttctca accg                                          24

<210> SEQ ID NO 23
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 23
aacgaaattc tcaaagatgg gttt                                          24

<210> SEQ ID NO 24
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 24
aacgaaattc tcaaagatgg gttt                                          24

<210> SEQ ID NO 25
<211> LENGTH: 23
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 25
cgtcacacca tccacaccac ttg                                           23

<210> SEQ ID NO 26
<211> LENGTH: 26
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 26
gacggcaata cttatcgcca acatat                                        26

<210> SEQ ID NO 27
<211> LENGTH: 26
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 27
aattggacca gatgggattg ggaaag                                        26
```

<210> SEQ ID NO 28
<211> LENGTH: 28
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 28
tccacacaaa aatgtcagag tgcttagc                                        28

<210> SEQ ID NO 29
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 29
cttgattact ggcacaccta tcca                                            24

<210> SEQ ID NO 30
<211> LENGTH: 22
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 30
gggaaaagag gaggacacga tg                                              22

<210> SEQ ID NO 31
<211> LENGTH: 26
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 31
tgtttatctc cctatctatt tccttg                                          26

<210> SEQ ID NO 32
<211> LENGTH: 21
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 32
ctttctctct gccctcctca a                                               21

<210> SEQ ID NO 33
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 33
tggaatacat cggcatagag aaag                                            24

<210> SEQ ID NO 34

```
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 34
taaactcgga tgctcggtga taag                                           24

<210> SEQ ID NO 35
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 35
ccaggaaaaa ggcagaagag aaga                                           24

<210> SEQ ID NO 36
<211> LENGTH: 24
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 36
cattgtgtga ttcagggaga tcga                                           24

<210> SEQ ID NO 37
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 37
gggcgttttt cccagtgttg                                                20

<210> SEQ ID NO 38
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 38
tcagcccgca gagaatgaat                                                20

<210> SEQ ID NO 39
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 39
tcccacccac acctgtttca                                                20

<210> SEQ ID NO 40
<211> LENGTH: 20
```

-continued

```
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 40
ttccgcagca gccaacattt                                               20

<210> SEQ ID NO 41
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 41
gaagccaagg aacaggagta                                               20

<210> SEQ ID NO 42
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 42
catacgggca cacacagata                                               20

<210> SEQ ID NO 43
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 43
ctcgcccatt gttgtttcag                                               20

<210> SEQ ID NO 44
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 44
aattgcggaa accatgttcc                                               20

<210> SEQ ID NO 45
<211> LENGTH: 20
<212> TYPE: DNA
<213> ORGANISM: Artificial Sequence
<220> FEATURE:
<223> OTHER INFORMATION: primer used for ANG4 candidate genes
      amplification and sequencing (table 9)

<400> SEQUENCE: 45
tggggcatta gaactggaac                                               20

<210> SEQ ID NO 46
<211> LENGTH: 20
<212> TYPE: DNA
```

-continued

<213> ORGANISM: Artificial Sequence
<220> FEATURE:
<223> OTHER INFORMATION: primer used for ANG4 candidate genes
      amplification and sequencing (table 9)

<400> SEQUENCE: 46
tcccaaggat cgaagtcttt                                              20

<210> SEQ ID NO 47
<211> LENGTH: 52
<212> TYPE: DNA
<213> ORGANISM: Arabidopsis thaliana
<220> FEATURE:
<221> NAME/KEY: misc_feature
<223> OTHER INFORMATION: Aligned Ang sequence in fig 8

<400> SEQUENCE: 47
aatcatcaag aattgaagat taggtatatc tgtgtgtgcc cgtatgctca aa          52

<210> SEQ ID NO 48
<211> LENGTH: 52
<212> TYPE: DNA
<213> ORGANISM: Arabidopsis thaliana
<220> FEATURE:
<221> NAME/KEY: misc_feature
<223> OTHER INFORMATION: Aligned Ler sequence in fig 8

<400> SEQUENCE: 48
aatcatcaag aattgaagat caggtatatc tgtgtgtgcc cgtatgctca aa          52

<210> SEQ ID NO 49
<211> LENGTH: 1002
<212> TYPE: PRT
<213> ORGANISM: Homo sapiens
<220> FEATURE:
<221> NAME/KEY: MISC_FEATURE
<223> OTHER INFORMATION: AAP36593.1 in Fig. 10

<400> SEQUENCE: 49

Met Ser Gly Pro Gly Asn Lys Arg Ala Ala Gly Asp Gly Ser Gly
1               5                   10                  15

Pro Pro Glu Lys Lys Leu Ser Arg Glu Glu Lys Thr Thr Thr Leu
                20                  25                  30

Ile Glu Pro Ile Arg Leu Gly Gly Ile Ser Ser Thr Glu Met Asp
            35                  40                  45

Leu Lys Val Leu Gln Phe Lys Asn Lys Lys Leu Ala Glu Arg Leu
        50                  55                  60

Gln Arg Gln Ala Cys Glu Asp Glu Leu Arg Glu Arg Ile Glu Lys Leu
65                  70                  75                  80

Glu Lys Arg Gln Ala Thr Asp Asp Ala Thr Leu Leu Ile Val Asn Arg
                85                  90                  95

Tyr Trp Ala Gln Leu Asp Glu Thr Val Glu Ala Leu Leu Arg Cys His
                100                 105                 110

Glu Ser Gln Gly Glu Leu Ser Ser Ala Pro Glu Ala Pro Gly Thr Gln
            115                 120                 125

Glu Gly Pro Thr Cys Asp Gly Thr Pro Leu Pro Glu Pro Gly Thr Ser
        130                 135                 140

Glu Leu Arg Asp Pro Leu Leu Met Gln Leu Arg Pro Pro Leu Ser Glu
145                 150                 155                 160

Pro Ala Leu Ala Phe Val Val Ala Leu Gly Ala Ser Ser Ser Glu Glu
                165                 170                 175

-continued

```
Val Glu Leu Glu Leu Gln Gly Arg Met Glu Phe Ser Lys Ala Ala Val
            180                 185                 190
Ser Arg Val Val Glu Ala Ser Asp Arg Leu Gln Arg Val Glu Glu
        195                 200                 205
Leu Cys Gln Arg Val Tyr Ser Arg Gly Asp Ser Glu Pro Leu Ser Glu
    210                 215                 220
Ala Ala Gln Ala His Thr Arg Glu Leu Gly Arg Glu Asn Arg Arg Leu
225                 230                 235                 240
Gln Asp Leu Ala Thr Gln Leu Gln Glu Lys His His Arg Ile Ser Leu
                245                 250                 255
Glu Tyr Ser Glu Leu Gln Asp Lys Val Thr Ser Ala Glu Thr Lys Val
            260                 265                 270
Leu Glu Met Glu Thr Thr Val Glu Asp Leu Gln Trp Asp Ile Glu Lys
        275                 280                 285
Leu Arg Lys Arg Glu Gln Lys Leu Asn Lys His Leu Ala Glu Ala Leu
    290                 295                 300
Glu Gln Leu Asn Ser Gly Tyr Tyr Val Ser Gly Ser Ser Ser Gly Phe
305                 310                 315                 320
Gln Gly Gly Gln Ile Thr Leu Ser Met Gln Lys Phe Glu Met Leu Asn
                325                 330                 335
Ala Glu Leu Glu Glu Asn Gln Glu Leu Ala Asn Ser Arg Met Ala Glu
            340                 345                 350
Leu Glu Lys Leu Gln Ala Glu Leu Gln Gly Ala Val Arg Thr Asn Glu
        355                 360                 365
Arg Leu Lys Val Ala Leu Arg Ser Leu Pro Glu Glu Val Val Arg Glu
    370                 375                 380
Thr Gly Glu Tyr Arg Met Leu Gln Ala Gln Phe Ser Leu Leu Tyr Asn
385                 390                 395                 400
Glu Ser Leu Gln Val Lys Thr Gln Leu Asp Glu Ala Arg Gly Leu Leu
                405                 410                 415
Leu Ala Thr Lys Asn Ser His Leu Arg His Ile Glu His Met Glu Ser
            420                 425                 430
Asp Glu Leu Gly Leu Gln Lys Lys Leu Arg Thr Glu Val Ile Gln Leu
        435                 440                 445
Glu Asp Thr Leu Ala Gln Val Arg Lys Glu Tyr Glu Met Leu Arg Ile
    450                 455                 460
Glu Phe Glu Gln Asn Leu Ala Ala Asn Glu Gln Ala Gly Pro Ile Asn
465                 470                 475                 480
Arg Glu Met Arg His Leu Ile Ser Ser Leu Gln Asn His Asn His Gln
                485                 490                 495
Leu Lys Gly Asp Ala Gln Arg Tyr Lys Arg Lys Leu Arg Glu Val Gln
            500                 505                 510
Ala Glu Ile Gly Lys Leu Arg Ala Gln Ala Ser Gly Ser Ala His Ser
        515                 520                 525
Thr Pro Asn Leu Gly His Pro Glu Asp Ser Gly Val Ser Ala Pro Ala
    530                 535                 540
Pro Gly Lys Glu Glu Gly Gly Pro Gly Pro Val Ser Thr Pro Asp Asn
545                 550                 555                 560
Arg Lys Glu Met Ala Pro Val Pro Gly Thr Thr Thr Thr Thr Thr Ser
                565                 570                 575
Val Lys Lys Glu Glu Leu Val Pro Ser Glu Asp Phe Gln Gly Ile
            580                 585                 590
Thr Pro Gly Ala Gln Gly Pro Ser Ser Arg Gly Arg Glu Pro Glu Ala
```

-continued

```
                595                 600                 605
Arg Pro Lys Arg Glu Leu Arg Glu Arg Glu Gly Pro Ser Leu Gly Pro
    610                 615                 620

Pro Pro Val Ala Ser Ala Leu Ser Arg Ala Asp Arg Glu Lys Ala Lys
625                 630                 635                 640

Val Glu Glu Thr Lys Arg Lys Glu Ser Glu Leu Leu Lys Gly Leu Arg
                645                 650                 655

Ala Glu Leu Lys Lys Ala Gln Glu Ser Gln Lys Glu Met Lys Leu Leu
            660                 665                 670

Leu Asp Met Tyr Lys Ser Ala Pro Lys Glu Gln Arg Asp Lys Val Gln
            675                 680                 685

Leu Met Ala Ala Glu Arg Lys Ala Lys Ala Glu Val Asp Glu Leu Arg
            690                 695                 700

Ser Arg Ile Arg Glu Leu Glu Arg Asp Arg Glu Ser Lys Lys
705                 710                 715                 720

Ile Ala Asp Glu Asp Ala Leu Arg Arg Ile Arg Gln Ala Glu Glu Gln
                725                 730                 735

Ile Glu His Leu Gln Arg Lys Leu Gly Ala Thr Lys Gln Glu Glu Glu
            740                 745                 750

Ala Leu Leu Ser Glu Met Asp Val Thr Gly Gln Ala Phe Glu Asp Met
            755                 760                 765

Gln Glu Gln Asn Gly Arg Leu Leu Gln Gln Leu Arg Glu Lys Asp Asp
            770                 775                 780

Ala Asn Phe Lys Leu Met Ser Glu Arg Ile Lys Ala Asn Gln Ile His
785                 790                 795                 800

Lys Leu Leu Arg Glu Glu Lys Asp Glu Leu Gly Glu Gln Val Leu Gly
                805                 810                 815

Leu Lys Ser Gln Val Asp Ala Gln Leu Leu Thr Val Gln Lys Leu Glu
            820                 825                 830

Glu Lys Glu Arg Ala Leu Gln Gly Ser Leu Gly Gly Val Glu Lys Glu
            835                 840                 845

Leu Thr Leu Arg Ser Gln Ala Leu Glu Leu Asn Lys Arg Lys Ala Val
            850                 855                 860

Glu Ala Ala Gln Leu Ala Glu Asp Leu Lys Val Gln Leu Glu His Val
865                 870                 875                 880

Gln Thr Arg Leu Arg Glu Ile Gln Pro Cys Leu Ala Glu Ser Arg Ala
                885                 890                 895

Ala Arg Glu Lys Glu Ser Phe Asn Leu Lys Arg Ala Gln Glu Asp Ile
            900                 905                 910

Ser Arg Leu Arg Arg Lys Leu Glu Lys Gln Arg Lys Val Glu Val Tyr
            915                 920                 925

Ala Asp Ala Asp Glu Ile Leu Gln Glu Ile Lys Glu Tyr Lys Ala
            930                 935                 940

Arg Leu Thr Cys Pro Cys Cys Asn Thr Arg Lys Lys Asp Ala Val Leu
945                 950                 955                 960

Thr Lys Cys Phe His Val Phe Cys Phe Glu Cys Val Arg Gly Arg Tyr
                965                 970                 975

Glu Ala Arg Gln Arg Lys Cys Pro Lys Cys Asn Ala Ala Phe Gly Ala
            980                 985                 990

His Asp Phe His Arg Ile Tyr Ile  Ser Leu
            995                 1000
```

<210> SEQ ID NO 50

-continued

```
<211> LENGTH: 975
<212> TYPE: PRT
<213> ORGANISM: Homo sapiens
<220> FEATURE:
<221> NAME/KEY: MISC_FEATURE
<223> OTHER INFORMATION: AAK58539_RFP_20 in Fig. 10

<400> SEQUENCE: 50

Met Ser Gly Ile Gly Asn Lys Arg Ala Ala Gly Glu Pro Gly Thr Ser
1               5                   10                  15

Met Pro Pro Glu Lys Lys Ala Ala Val Glu Asp Ser Gly Thr Thr Val
            20                  25                  30

Glu Thr Ile Lys Leu Gly Gly Val Ser Ser Thr Glu Leu Asp Ile
        35                  40                  45

Arg Thr Leu Gln Thr Lys Asn Arg Lys Leu Ala Glu Met Leu Asp Gln
    50                  55                  60

Arg Gln Ala Ile Glu Asp Glu Leu Arg Glu His Ile Glu Lys Leu Glu
65                  70                  75                  80

Arg Arg Gln Ala Thr Asp Asp Ala Ser Leu Leu Ile Val Asn Arg Tyr
                85                  90                  95

Trp Ser Gln Phe Asp Glu Asn Ile Arg Ile Ile Leu Lys Arg Tyr Asp
            100                 105                 110

Leu Glu Gln Gly Leu Gly Asp Leu Leu Thr Glu Arg Lys Ala Leu Val
        115                 120                 125

Val Pro Glu Pro Glu Pro Asp Ser Asp Ser Asn Gln Glu Arg Lys Asp
    130                 135                 140

Asp Arg Glu Arg Gly Glu Gly Gln Glu Pro Ala Phe Ser Phe Leu Ala
145                 150                 155                 160

Thr Leu Ala Ser Ser Ser Glu Glu Met Glu Ser Gln Leu Gln Glu
                165                 170                 175

Arg Val Glu Ser Ser Arg Arg Ala Val Ser Gln Ile Val Thr Val Tyr
            180                 185                 190

Asp Lys Leu Gln Glu Lys Val Glu Leu Leu Ser Arg Lys Leu Asn Ser
        195                 200                 205

Gly Asp Asn Leu Ile Val Glu Glu Ala Val Gln Glu Leu Asn Ser Phe
    210                 215                 220

Leu Ala Gln Glu Asn Met Arg Leu Gln Glu Leu Thr Asp Leu Leu Gln
225                 230                 235                 240

Glu Lys His Arg Thr Met Ser Gln Glu Phe Ser Lys Leu Gln Ser Lys
                245                 250                 255

Val Glu Thr Ala Glu Ser Arg Val Ser Val Leu Glu Ser Met Ile Asp
            260                 265                 270

Asp Leu Gln Trp Asp Ile Asp Lys Ile Arg Lys Arg Glu Gln Arg Leu
        275                 280                 285

Asp Arg His Leu Ala Glu Val Leu Glu Arg Val Asn Ser Lys Gly Tyr
    290                 295                 300

Lys Val Tyr Gly Ala Gly Ser Ser Leu Tyr Gly Gly Thr Ile Thr Ile
305                 310                 315                 320

Asn Ala Arg Lys Phe Glu Met Asn Ala Glu Leu Glu Glu Asn Lys
                325                 330                 335

Glu Leu Ala Gln Asn Arg Leu Cys Glu Leu Lys Leu Arg Gln Asp
            340                 345                 350

Phe Glu Glu Val Thr Thr Gln Asn Glu Lys Leu Lys Val Glu Leu Arg
        355                 360                 365

Ser Ala Val Glu Gln Val Val Lys Glu Thr Pro Glu Tyr Arg Cys Met
```

```
                370              375              380
Gln Ser Gln Phe Ser Val Leu Tyr Asn Glu Ser Leu Gln Leu Lys Ala
385                      390                      395                      400

His Leu Asp Glu Ala Arg Thr Leu Leu His Gly Thr Arg Gly Thr His
                405                      410                      415

Gln His Gln Val Glu Leu Ile Glu Arg Asp Glu Val Ser Leu His Lys
                420                      425                      430

Lys Leu Arg Thr Glu Val Ile Gln Leu Glu Asp Thr Leu Ala Gln Val
                435                      440                      445

Arg Lys Glu Tyr Glu Met Leu Arg Ile Glu Phe Glu Gln Thr Leu Ala
450                      455                      460

Ala Asn Glu Gln Ala Gly Pro Ile Asn Arg Glu Met Arg His Leu Ile
465                      470                      475                      480

Ser Ser Leu Gln Asn His Asn His Gln Leu Lys Gly Glu Val Leu Arg
                485                      490                      495

Tyr Lys Arg Lys Leu Arg Glu Ala Gln Ser Asp Leu Asn Lys Thr Arg
                500                      505                      510

Leu Arg Ser Gly Ser Ala Leu Leu Gln Ser Gln Ser Ser Thr Glu Asp
                515                      520                      525

Pro Lys Asp Glu Pro Ala Glu Leu Lys Pro Asp Ser Glu Asp Leu Ser
                530                      535                      540

Ser Gln Ser Ser Ala Ser Lys Ala Ser Gln Glu Asp Ala Asn Glu Ile
545                      550                      555                      560

Lys Ser Lys Arg Asp Glu Glu Arg Glu Arg Glu Arg Arg Glu Lys
                565                      570                      575

Glu Arg Glu Arg Glu Arg Glu Arg Glu Lys Glu Lys Glu Arg Glu Arg
                580                      585                      590

Glu Lys Gln Lys Leu Lys Glu Ser Glu Lys Glu Arg Asp Ser Ala Lys
                595                      600                      605

Asp Lys Glu Lys Gly Lys His Asp Asp Gly Arg Lys Lys Glu Ala Glu
                610                      615                      620

Ile Ile Lys Gln Leu Lys Ile Glu Leu Lys Lys Ala Gln Glu Ser Gln
625                      630                      635                      640

Lys Glu Met Lys Leu Leu Leu Asp Met Tyr Arg Ser Ala Pro Lys Glu
                645                      650                      655

Gln Arg Asp Lys Val Gln Leu Met Ala Ala Glu Lys Lys Ser Lys Ala
                660                      665                      670

Glu Leu Glu Asp Leu Arg Gln Arg Leu Lys Asp Leu Glu Asp Lys Glu
                675                      680                      685

Lys Lys Glu Asn Thr Lys Met Ala Asp Glu Asp Ala Leu Arg Lys Ile
                690                      695                      700

Arg Ala Val Glu Glu Gln Ile Glu Tyr Leu Gln Lys Lys Leu Ala Met
705                      710                      715                      720

Ala Lys Gln Glu Glu Glu Ala Leu Leu Ser Glu Met Asp Val Thr Gly
                725                      730                      735

Gln Ala Phe Glu Asp Met Gln Glu Gln Asn Ile Arg Leu Met Gln Gln
                740                      745                      750

Leu Arg Glu Lys Asp Asp Ala Asn Phe Lys Leu Met Ser Glu Arg Ile
                755                      760                      765

Lys Ser Asn Gln Ile His Lys Leu Leu Lys Glu Glu Lys Glu Glu Leu
                770                      775                      780

Ala Asp Gln Val Leu Thr Leu Lys Thr Gln Val Asp Ala Gln Leu Gln
785                      790                      795                      800
```

```
Val Val Arg Lys Leu Glu Glu Lys Glu His Leu Leu Gln Ser Asn Ile
            805                 810                 815
Gly Thr Gly Glu Lys Glu Leu Gly Leu Arg Thr Gln Ala Leu Glu Met
        820                 825                 830
Asn Lys Arg Lys Ala Met Glu Ala Ala Gln Leu Ala Asp Asp Leu Lys
        835                 840                 845
Ala Gln Leu Glu Leu Ala Gln Lys Lys Leu His Asp Phe Gln Asp Glu
    850                 855                 860
Ile Val Glu Asn Ser Val Thr Lys Glu Lys Asp Met Phe Asn Phe Lys
865                 870                 875                 880
Arg Ala Gln Glu Asp Ile Ser Arg Leu Arg Arg Lys Leu Glu Thr Thr
                885                 890                 895
Lys Lys Pro Asp Asn Val Pro Lys Cys Asp Glu Ile Leu Met Glu Glu
            900                 905                 910
Ile Lys Asp Tyr Lys Ala Arg Leu Thr Cys Pro Cys Cys Asn Met Arg
        915                 920                 925
Lys Lys Asp Ala Val Leu Thr Lys Cys Phe His Val Phe Cys Phe Glu
    930                 935                 940
Cys Val Lys Thr Arg Tyr Asp Thr Arg Gln Arg Lys Cys Pro Lys Cys
945                 950                 955                 960
Asn Ala Ala Phe Gly Ala Asn Asp Phe His Arg Ile Tyr Ile Gly
                965                 970                 975

<210> SEQ ID NO 51
<211> LENGTH: 883
<212> TYPE: PRT
<213> ORGANISM: Oryza sativa
<220> FEATURE:
<221> NAME/KEY: MISC_FEATURE
<223> OTHER INFORMATION: CAD41603.3 in Fig. 10

<400> SEQUENCE: 51

Met Gly Ser Thr Gly Glu Pro Asp Arg Lys Arg Arg Leu Ser Ser Ser
1               5                   10                  15
Val Ala Pro Gly Gly Ala Pro Val Ser Pro Ala Lys Arg Leu Ala
            20                  25                  30
Val Ala Pro Thr Ser Glu Asp Lys Lys Leu Asp Phe Thr Val Leu Lys
        35                  40                  45
Tyr Lys Asn Gln Lys Leu Ser Glu Gln Leu Glu Ala His Lys Phe Glu
    50                  55                  60
Tyr Arg Ala Leu Glu Asn Lys Phe Ala Gly Leu Lys Glu Lys Gln Arg
65                  70                  75                  80
Thr His Asn Glu Thr Leu Ser Leu Val Asn Ser Ser Trp Glu Gln Leu
                85                  90                  95
Val Ala Asp Leu Lys Ser Arg Ser Phe Cys Lys Ser Gly Ser Pro Asn
            100                 105                 110
Ser Ser Pro Gly Ser Gly His Asn Asn Val Gln Lys Asp Gly Thr Cys
        115                 120                 125
Ala Pro Ile Glu Arg Asp Thr Leu Arg Ser Leu Val Glu Ser Gly Ala
    130                 135                 140
Thr Glu Ser Ser Gly Cys Leu Pro Gly Cys His Leu Gly Ser Asp Ala
145                 150                 155                 160
Pro Pro Leu His Leu Ser Thr Ala Asn Ala Leu Gly Asp Ile Phe Phe
                165                 170                 175
Pro Ser Ser Asp Leu Leu Gln Ala Asn Glu Glu Cys Ala Leu Ala Ala
```

```
                180                 185                 190
Leu Thr Lys Leu Pro Glu Asn Asp Arg Ser Lys Gln Leu Gln Ser Thr
            195                 200                 205

Ser Ser Asn Leu Leu Ser Ser Leu Asn Asn Val Val Gln Ala Leu Ser
        210                 215                 220

Asn Leu Gln Leu Lys His Lys Gln Leu Ala Glu Asp Tyr Gln Asn Gln
225                 230                 235                 240

Arg Asp Ser Ser Ala Arg Lys Arg Ala Glu His Arg Arg Leu Lys Glu
                245                 250                 255

Glu Leu Ala Ser Ala Ser Glu Leu Glu Glu Thr Asn Tyr Lys Leu
            260                 265                 270

Ala Ala Leu Lys Ala Gln Arg Asp Asn Thr Gln Gly Ala Arg Ile Pro
        275                 280                 285

Tyr Pro Thr Leu Gly Asn Lys Asn Met Pro Glu Asp Lys Glu Leu Ile
    290                 295                 300

Ser Lys Arg Leu Val Glu Ile Lys Arg Leu His Glu Glu Arg Ile Glu
305                 310                 315                 320

Ile Leu Asn Lys Ile Ala Thr Phe Gln Asn Ile Leu Met Asp Phe Lys
                325                 330                 335

Ser Ile Arg Ser Ser Lys Ala Phe Gln Leu Val Asn Asp Arg Leu Gln
            340                 345                 350

Lys Ser Gln Ala Glu Leu Asp His Tyr Gln Thr Leu Leu Glu Lys Leu
        355                 360                 365

Gln Val Asp Lys Asp Lys Phe Val Trp Gln Arg Gln Phe Asn Leu
    370                 375                 380

Lys Val Asp Leu Ala Glu Ile Pro Glu Arg Val Ser Thr Tyr Cys Arg
385                 390                 395                 400

Asn Gln Val Ile Thr Lys Phe Lys Ala Leu Val Ser Ser Ile Pro Arg
                405                 410                 415

Glu Met Gly Ala Met Gln Ser Glu Met Thr Lys His Lys Glu Ala Ser
            420                 425                 430

Leu Glu Leu Asn Ser Leu Arg Ala Glu Val His Ser Leu Ser Arg Ile
        435                 440                 445

Leu Ser Arg Lys Glu Arg Asp Asn Glu Glu Ala Ser Cys Arg Ser Ala
    450                 455                 460

Arg Ala Gly Ser Asp Ile Thr Gln Leu Gln Ser Val Ile Ser Asp Leu
465                 470                 475                 480

Lys Gln Thr Asn Lys Glu Leu Lys Leu Phe Ala Asp Met Tyr Lys Arg
                485                 490                 495

Glu Ser Thr Asp Ser Arg Glu Ile Met Glu Ser Arg Asp Arg Glu Phe
            500                 505                 510

Leu Glu Trp Ala His Val His Ala Leu Lys Ser Ser Leu Asp Glu Ser
        515                 520                 525

Lys Leu Glu Gln Arg Val Lys Ala Ala Asn Glu Ala Glu Ala Ile Thr
    530                 535                 540

Gln Gln Arg Leu Ala Thr Ala Glu Ala Glu Ile Ala Glu Ser Gly Gln
545                 550                 555                 560

Lys Leu Gly Thr Ser Arg Lys Tyr Arg Ile Met Leu Leu Asn Ile Val
                565                 570                 575

Ser Leu Arg Thr Val Glu Val Gly Val Thr Ser Leu Leu Gly Asp Leu
            580                 585                 590

Val Ser Leu Ser His Met Leu Lys Ser Lys Gln Glu Glu Cys Glu Ala
        595                 600                 605
```

-continued

Tyr Arg Val Glu Val Glu Cys Ile Gly Gln Ala Tyr Glu Asp Ile Gln
    610                 615                 620

Ala Gln Asn Gln Gln Leu Leu Gln Gln Ile Ile Glu Arg Asp Asp Asp
625                 630                 635                 640

Asn Thr Lys Asp Val Arg Phe Gly Tyr Ile Val Asn Leu Ile Val Pro
                645                 650                 655

Glu Thr Gln Tyr Phe Ile Glu Lys Leu Phe Thr Cys Val Lys Leu Ile
            660                 665                 670

Phe Met Glu Gly Val Lys Ala Lys Gln Thr Gln Asp Ala Leu His Leu
        675                 680                 685

Glu Thr Tyr Ser Leu Arg Arg Asn Leu Gln Gln Glu Ser Ser Leu Met
    690                 695                 700

Asp Leu Tyr Asn Gln Lys Ile Val Ser Leu Glu Asp Gln Leu Lys Met
705                 710                 715                 720

Trp Ser Asp Arg Val Gly Lys Leu Gln Glu Asp Gly Trp Gln Gln Ser
                725                 730                 735

Val Ser Leu Ser Asn Tyr Gln Arg Lys Leu Val Asp Val His Arg Asp
            740                 745                 750

Ala Gln Lys Leu Met Gln Ser Leu Asp Gly Ile Gln Ala Asn Val Gly
        755                 760                 765

Ser Ser Arg Leu Glu Val Ala Asp Leu Leu Ile Glu Leu Glu Lys Glu
    770                 775                 780

Arg Phe Ser Lys Lys Arg Ile Glu Asp Asp Leu Glu Val Met Ser Arg
785                 790                 795                 800

Lys Ala Ser Ser Leu Arg Ala Lys Ala Arg Glu Ser Ala Val Leu Glu
                805                 810                 815

Lys Leu Arg His Glu Val Lys Glu Tyr Arg Gly Ile Leu Lys Cys Gly
            820                 825                 830

Ile Cys His Asp Arg Gln Lys Glu Val Val Ile Thr Lys Cys Tyr His
        835                 840                 845

Leu Phe Cys Asn Gln Cys Ile Gln Lys Ser Leu Gly Asn Arg Gln Arg
    850                 855                 860

Arg Cys Pro Ser Cys Ser Leu Ser Phe Gly Ala Asn Asp Val Lys Pro
865                 870                 875                 880

Ile Tyr Ile

<210> SEQ ID NO 52
<211> LENGTH: 899
<212> TYPE: PRT
<213> ORGANISM: Arabidopsis thaliana
<220> FEATURE:
<221> NAME/KEY: MISC_FEATURE
<223> OTHER INFORMATION: MIPS_At1g55250 in Fig. 10

<400> SEQUENCE: 52

Met Glu Asn Gln Glu Ser Asp Glu Pro Met Gln Lys Lys Pro His Leu
1               5                   10                  15

Leu Asp Ser Val Ser Pro Asn Ser Met Ala Arg Asn Ser Ser Pro Ser
            20                  25                  30

His Pro Ile Ala Lys Ser Val Ser Phe Phe Asp Cys Asp Phe Ser Leu
        35                  40                  45

Leu Cys Leu Arg Leu Val Asp Tyr Glu Ile Asp Val Asp Ala Thr Val
    50                  55                  60

Leu Gln Leu Gln Asn Gln Lys Leu Val Gln Gln Leu Asp Leu Gln Lys
65                  70                  75                  80

```
Lys Gln Leu Tyr Asp Val Glu Ser Lys Ile Gln Glu Leu Gln Leu Asn
                85                  90                  95
Gln Thr Ser Tyr Asp Glu Leu Ile Ser Val Asn Gln Leu Trp Asn
            100                 105                 110
Gln Leu Val Asp Asp Leu Ile Leu Leu Gly Val Arg Ala Gly Ala Asn
            115                 120                 125
Gln Glu Ala Leu Asn Tyr Leu Asp Ile Val Asp Lys Lys Arg Val Pro
    130                 135                 140
Pro Cys Ala Ala Asp Glu Thr Phe Leu Cys Arg Leu Leu Gln Val Asp
145                 150                 155                 160
Ser Leu Asp Thr Ser Lys Ser Asp Glu Val Val Arg Lys Val Glu Glu
                165                 170                 175
Ala Leu Ala Leu Arg His Ser Ser Thr Met Glu Leu Met Gly Leu Phe
            180                 185                 190
Glu Asn Thr Ile Asp Thr Gln Lys Thr Lys Ala Glu Ser Ile Ser Gln
            195                 200                 205
Ser Leu His Ala Val Lys Ser Thr Glu Asp Ala Thr Ile Gln Leu Ser
    210                 215                 220
Ser Ile Asn Asp Leu Met Lys Glu Ser Lys Asn Leu Arg Glu Met
225                 230                 235                 240
Ile Asp Ala Leu His Val Arg His Lys Glu His Ser Glu Gln Ile Gln
                245                 250                 255
Ala Tyr Ile Ser Ser His Ser Thr Asp Gln Ser Glu Leu Lys His Leu
            260                 265                 270
Lys Gly Gln Leu Glu Glu Ile Lys Ala Glu Leu Glu Glu Asn Arg Arg
            275                 280                 285
Lys Leu Ile Thr Leu Lys Met Gln Lys Asp Ala Ala Cys Glu Gly His
    290                 295                 300
Val Thr Ser Pro Ala Ile Ala Asn Gly Ser Leu Ser Pro Glu Lys Pro
305                 310                 315                 320
Val Asp Lys Thr Lys Leu Arg Glu Leu Lys Asp Ser Ile Asp Glu Ile
                325                 330                 335
Lys Ile Met Ala Glu Gly Arg Leu Ser Glu Leu Gln Ala Ser Gln Glu
            340                 345                 350
Tyr Asn Leu Ser Leu Ser Arg Gln Cys Gln Asp Ile Glu Asn Glu Leu
            355                 360                 365
Lys Asp Asp Gln Tyr Ile Tyr Ser Ser Arg Leu Tyr Ser Leu Ile Asn
    370                 375                 380
Asp Arg Ile His His Trp Asn Ala Glu Leu Asp Arg Tyr Lys Ile Leu
385                 390                 395                 400
Thr Glu Ala Ile Gln Ala Glu Arg Ser Phe Val Met Arg Arg Asp Lys
                405                 410                 415
Glu Leu Asn Leu Arg Ala Glu Ser Leu Glu Ala Ala Asn His Lys Thr
            420                 425                 430
Thr Thr Val Gly Ser Arg Ile Glu Val Leu Glu Lys Lys Leu Gln Ser
            435                 440                 445
Cys Ile Ile Glu Lys Asn Gly Leu Glu Leu Glu Thr Glu Glu Ala Ile
    450                 455                 460
Gln Asp Ser Glu Arg Gln Asp Ile Lys Ser Glu Phe Ile Ala Met Ala
465                 470                 475                 480
Ser Thr Leu Ser Lys Glu Met Glu Met Met Glu Ala Gln Leu Lys Arg
                485                 490                 495
```

```
Trp Lys Asp Thr Ala Gln Asp Ala Leu Tyr Leu Arg Glu Gln Ala Gln
            500                 505                 510

Ser Leu Arg Val Ser Leu Ser Asn Lys Ala Asp Glu Gln Lys Gly Leu
            515                 520                 525

Glu Asp Lys Cys Ala Lys Gln Met Ala Glu Ile Lys Ser Leu Lys Ala
            530                 535                 540

Leu Ile Glu Lys Leu Leu Lys Glu Lys Leu Gln Leu Gln Asn Leu Ala
545                 550                 555                 560

Ser Ile Cys Thr Arg Glu Cys Asn Asp Asp Arg Gly Leu Ala Glu Ile
            565                 570                 575

Lys Asp Ser Gln Arg Lys Ala Gln Ala Gln Ala Glu Leu Lys Asn
            580                 585                 590

Val Leu Asp Glu His Phe Leu Glu Leu Arg Val Lys Ala Ala His Glu
            595                 600                 605

Thr Glu Ser Ala Cys Gln Glu Arg Leu Ala Thr Ala Lys Ala Glu Ile
            610                 615                 620

Ala Glu Leu Arg Thr Gln Leu Asp Leu Ser Glu Arg Glu Val Leu Glu
625                 630                 635                 640

Leu Lys Glu Gly Ile Lys Val Lys Glu Gln Ala Glu Ala Ser Ile
            645                 650                 655

Ala Glu Met Glu Thr Ile Gly Gln Ala Tyr Glu Asp Met Gln Thr Gln
            660                 665                 670

Asn Gln His Leu Leu Gln Gln Val Ala Glu Arg Asp Asp Tyr Asn Ile
            675                 680                 685

Lys Leu Val Ser Glu Ser Val Lys Thr Lys His Ala Tyr Asn Thr His
            690                 695                 700

Leu Ser Glu Lys Gln Val Met Glu Lys Gln Leu His Gln Val Asn Ala
705                 710                 715                 720

Ser Val Glu Asn Phe Lys Ala Arg Ile Ala His Asn Glu Glu Gln Met
            725                 730                 735

Lys Gly Cys Phe Ser Glu Ala Tyr Lys Leu Ile Gln Glu Asp Arg His
            740                 745                 750

Leu Val Ile Ser Leu Glu Thr Thr Lys Trp Glu Val Ala Asp Ala Asp
            755                 760                 765

Lys Glu Phe Arg Trp Leu Lys Ser Ala Val Ser Ser Ser Lys Glu
            770                 775                 780

Tyr Glu Gln Ile Ser Arg Arg Thr Asp Asp Ile Lys Leu Glu Leu Asp
785                 790                 795                 800

Asp Glu Arg Glu Lys Lys Leu Glu Glu Leu Met Glu Leu Asn
            805                 810                 815

Lys Glu Leu Glu Glu Leu Gly Ser Glu Ser Val Glu Ala Ala Ile Val
            820                 825                 830

Arg Leu Gln Glu Glu Val Lys Asn Cys Lys Asn Ile Leu Lys Cys Gly
            835                 840                 845

Val Cys Phe Asp Arg Pro Lys Glu Val Val Ile Val Lys Cys Tyr His
            850                 855                 860

Leu Phe Cys Gln Gln Cys Ile Gln Arg Ser Leu Glu Ile Arg His Arg
865                 870                 875                 880

Lys Cys Pro Gly Cys Gly Thr Ala Phe Gly Gln Asn Asp Val Arg Leu
            885                 890                 895

Val Lys Met
```

<210> SEQ ID NO 53

```
<211> LENGTH: 1001
<212> TYPE: PRT
<213> ORGANISM: Homo sapiens
<220> FEATURE:
<221> NAME/KEY: MISC_FEATURE
<223> OTHER INFORMATION: NP055586_RFP_40 in Fig. 10

<400> SEQUENCE: 53
```

| Met | Ser | Gly | Pro | Gly | Asn | Lys | Arg | Ala | Ala | Gly | Asp | Gly | Ser | Gly |
|---|---|---|---|---|---|---|---|---|---|---|---|---|---|---|
| 1 | | | | 5 | | | | | 10 | | | | | 15 |

| Pro | Pro | Glu | Lys | Lys | Leu | Ser | Arg | Glu | Glu | Lys | Thr | Thr | Thr | Leu |
|---|---|---|---|---|---|---|---|---|---|---|---|---|---|---|
| | | | 20 | | | | | 25 | | | | | 30 | |

| Ile | Glu | Pro | Ile | Arg | Leu | Gly | Gly | Ile | Ser | Ser | Thr | Glu | Met | Asp |
|---|---|---|---|---|---|---|---|---|---|---|---|---|---|---|
| | | 35 | | | | | 40 | | | | | 45 | | |

| Leu | Lys | Val | Leu | Gln | Phe | Lys | Asn | Lys | Lys | Leu | Ala | Glu | Arg | Leu | Glu |
|---|---|---|---|---|---|---|---|---|---|---|---|---|---|---|---|
| | 50 | | | | | 55 | | | | | 60 | | | | |

| Gln | Arg | Gln | Ala | Cys | Glu | Asp | Glu | Leu | Arg | Glu | Arg | Ile | Glu | Lys | Leu |
|---|---|---|---|---|---|---|---|---|---|---|---|---|---|---|---|
| 65 | | | | | 70 | | | | | 75 | | | | | 80 |

| Glu | Lys | Arg | Gln | Ala | Thr | Asp | Asp | Ala | Thr | Leu | Leu | Ile | Val | Asn | Arg |
|---|---|---|---|---|---|---|---|---|---|---|---|---|---|---|---|
| | | | | 85 | | | | | 90 | | | | | 95 | |

| Tyr | Trp | Ala | Gln | Leu | Asp | Glu | Thr | Val | Glu | Ala | Leu | Leu | Arg | Cys | His |
|---|---|---|---|---|---|---|---|---|---|---|---|---|---|---|---|
| | | | 100 | | | | | 105 | | | | | 110 | | |

| Glu | Ser | Gln | Gly | Glu | Leu | Ser | Ser | Ala | Pro | Glu | Ala | Pro | Gly | Thr | Gln |
|---|---|---|---|---|---|---|---|---|---|---|---|---|---|---|---|
| | | 115 | | | | | 120 | | | | | 125 | | | |

| Glu | Gly | Pro | Thr | Cys | Asp | Gly | Thr | Pro | Leu | Pro | Glu | Pro | Gly | Thr | Ser |
|---|---|---|---|---|---|---|---|---|---|---|---|---|---|---|---|
| | 130 | | | | | 135 | | | | | 140 | | | | |

| Glu | Leu | Arg | Asp | Pro | Leu | Leu | Met | Gln | Leu | Arg | Pro | Pro | Leu | Ser | Glu |
|---|---|---|---|---|---|---|---|---|---|---|---|---|---|---|---|
| 145 | | | | | 150 | | | | | 155 | | | | | 160 |

| Pro | Ala | Leu | Ala | Phe | Val | Val | Ala | Leu | Gly | Ala | Ser | Ser | Ser | Glu | Glu |
|---|---|---|---|---|---|---|---|---|---|---|---|---|---|---|---|
| | | | | 165 | | | | | 170 | | | | | 175 | |

| Val | Glu | Leu | Glu | Leu | Gln | Gly | Arg | Met | Glu | Phe | Ser | Lys | Ala | Ala | Val |
|---|---|---|---|---|---|---|---|---|---|---|---|---|---|---|---|
| | | | 180 | | | | | 185 | | | | | 190 | | |

| Ser | Arg | Val | Val | Glu | Ala | Ser | Asp | Arg | Leu | Gln | Arg | Arg | Val | Glu | Glu |
|---|---|---|---|---|---|---|---|---|---|---|---|---|---|---|---|
| | | 195 | | | | | 200 | | | | | 205 | | | |

| Leu | Cys | Gln | Arg | Val | Tyr | Ser | Arg | Gly | Asp | Ser | Glu | Pro | Leu | Ser | Glu |
|---|---|---|---|---|---|---|---|---|---|---|---|---|---|---|---|
| | 210 | | | | | 215 | | | | | 220 | | | | |

| Ala | Ala | Gln | Ala | His | Thr | Arg | Glu | Leu | Gly | Arg | Glu | Asn | Arg | Arg | Leu |
|---|---|---|---|---|---|---|---|---|---|---|---|---|---|---|---|
| 225 | | | | | 230 | | | | | 235 | | | | | 240 |

| Gln | Asp | Leu | Ala | Thr | Gln | Leu | Gln | Glu | Lys | His | His | Arg | Ile | Ser | Leu |
|---|---|---|---|---|---|---|---|---|---|---|---|---|---|---|---|
| | | | | 245 | | | | | 250 | | | | | 255 | |

| Glu | Tyr | Ser | Glu | Leu | Gln | Asp | Lys | Val | Thr | Ser | Ala | Glu | Thr | Lys | Val |
|---|---|---|---|---|---|---|---|---|---|---|---|---|---|---|---|
| | | | 260 | | | | | 265 | | | | | 270 | | |

| Leu | Glu | Met | Glu | Thr | Thr | Val | Glu | Asp | Leu | Gln | Trp | Asp | Ile | Glu | Lys |
|---|---|---|---|---|---|---|---|---|---|---|---|---|---|---|---|
| | | 275 | | | | | 280 | | | | | 285 | | | |

| Leu | Arg | Lys | Arg | Glu | Gln | Lys | Leu | Asn | Lys | His | Leu | Ala | Glu | Ala | Leu |
|---|---|---|---|---|---|---|---|---|---|---|---|---|---|---|---|
| | 290 | | | | | 295 | | | | | 300 | | | | |

| Glu | Gln | Leu | Asn | Ser | Gly | Tyr | Tyr | Val | Ser | Gly | Ser | Ser | Gly | Phe |
|---|---|---|---|---|---|---|---|---|---|---|---|---|---|---|
| 305 | | | | | 310 | | | | | 315 | | | | 320 |

| Gln | Gly | Gly | Gln | Ile | Thr | Leu | Ser | Met | Gln | Lys | Phe | Glu | Met | Leu | Asn |
|---|---|---|---|---|---|---|---|---|---|---|---|---|---|---|---|
| | | | | 325 | | | | | 330 | | | | | 335 | |

| Ala | Glu | Leu | Glu | Glu | Asn | Gln | Glu | Leu | Ala | Asn | Ser | Arg | Met | Ala | Glu |
|---|---|---|---|---|---|---|---|---|---|---|---|---|---|---|---|
| | | | 340 | | | | | 345 | | | | | 350 | | |

| Leu | Glu | Lys | Leu | Gln | Ala | Glu | Leu | Gln | Gly | Ala | Val | Arg | Thr | Asn | Glu |
|---|---|---|---|---|---|---|---|---|---|---|---|---|---|---|---|
| | | 355 | | | | | 360 | | | | | 365 | | | |

| Arg | Leu | Lys | Val | Ala | Leu | Arg | Ser | Leu | Pro | Glu | Glu | Val | Val | Arg | Glu |
|---|---|---|---|---|---|---|---|---|---|---|---|---|---|---|---|

```
                    370                 375                 380
Thr Gly Glu Tyr Arg Met Leu Gln Ala Gln Phe Ser Leu Leu Tyr Asn
385                 390                 395                 400
Glu Ser Leu Gln Val Lys Thr Gln Leu Asp Glu Ala Arg Gly Leu Leu
                    405                 410                 415
Leu Ala Thr Lys Asn Ser His Leu Arg His Ile Glu His Met Glu Ser
                420                 425                 430
Asp Glu Leu Gly Leu Gln Lys Lys Leu Arg Thr Glu Val Ile Gln Leu
                435                 440                 445
Glu Asp Thr Leu Ala Gln Val Arg Lys Glu Tyr Glu Met Leu Arg Ile
450                 455                 460
Glu Phe Glu Gln Asn Leu Ala Ala Asn Glu Gln Ala Gly Pro Ile Asn
465                 470                 475                 480
Arg Glu Met Arg His Leu Ile Ser Ser Leu Gln Asn His Asn His Gln
                485                 490                 495
Leu Lys Gly Asp Ala Gln Arg Tyr Lys Arg Lys Leu Arg Glu Val Gln
                500                 505                 510
Ala Glu Ile Gly Lys Leu Arg Ala Gln Ala Ser Gly Ser Ala His Ser
                515                 520                 525
Thr Pro Asn Leu Gly His Pro Glu Asp Ser Gly Val Ser Ala Pro Ala
                530                 535                 540
Pro Gly Lys Glu Glu Gly Gly Pro Gly Pro Val Ser Thr Pro Asp Asn
545                 550                 555                 560
Arg Lys Glu Met Ala Pro Val Pro Gly Thr Thr Thr Thr Thr Thr Ser
                565                 570                 575
Val Lys Lys Glu Glu Leu Val Pro Ser Glu Glu Asp Phe Gln Gly Ile
                580                 585                 590
Thr Pro Gly Ala Gln Gly Pro Ser Ser Arg Gly Arg Glu Pro Glu Ala
                595                 600                 605
Arg Pro Lys Arg Glu Leu Arg Glu Arg Glu Gly Pro Ser Leu Gly Pro
                610                 615                 620
Pro Pro Val Ala Ser Ala Leu Ser Arg Ala Asp Arg Glu Lys Ala Lys
625                 630                 635                 640
Val Glu Glu Thr Lys Arg Lys Glu Ser Glu Leu Leu Lys Gly Leu Arg
                645                 650                 655
Ala Glu Leu Lys Lys Ala Gln Glu Ser Gln Lys Glu Met Lys Leu Leu
                660                 665                 670
Leu Asp Met Tyr Lys Ser Ala Pro Lys Glu Gln Arg Asp Lys Val Gln
                675                 680                 685
Leu Met Ala Ala Glu Arg Lys Ala Lys Ala Glu Val Asp Glu Leu Arg
                690                 695                 700
Ser Arg Ile Arg Glu Leu Glu Glu Arg Asp Arg Glu Ser Lys Lys
705                 710                 715                 720
Ile Ala Asp Glu Asp Ala Leu Arg Arg Ile Arg Gln Ala Glu Glu Gln
                725                 730                 735
Ile Glu His Leu Gln Arg Lys Leu Gly Ala Thr Lys Gln Glu Glu Glu
                740                 745                 750
Ala Leu Leu Ser Glu Met Asp Val Thr Gly Gln Ala Phe Glu Asp Met
                755                 760                 765
Gln Glu Gln Asn Gly Arg Leu Leu Gln Gln Leu Arg Glu Lys Asp Asp
                770                 775                 780
Ala Asn Phe Lys Leu Met Ser Glu Arg Ile Lys Ala Asn Gln Ile His
785                 790                 795                 800
```

```
Lys Leu Leu Arg Glu Glu Lys Asp Glu Leu Gly Glu Gln Val Leu Gly
            805                 810                 815

Leu Lys Ser Gln Val Asp Ala Gln Leu Leu Thr Val Gln Lys Leu Glu
            820                 825                 830

Glu Lys Glu Arg Ala Leu Gln Gly Ser Leu Gly Gly Val Glu Lys Glu
            835                 840                 845

Leu Thr Leu Arg Ser Gln Ala Leu Glu Leu Asn Lys Arg Lys Ala Val
        850                 855                 860

Glu Ala Ala Gln Leu Ala Glu Asp Leu Lys Val Gln Leu Glu His Val
865                 870                 875                 880

Gln Thr Arg Leu Arg Glu Ile Gln Pro Cys Leu Ala Glu Ser Arg Ala
                885                 890                 895

Ala Arg Glu Lys Glu Ser Phe Asn Leu Lys Arg Ala Gln Glu Asp Ile
                900                 905                 910

Ser Arg Leu Arg Arg Lys Leu Glu Lys Gln Arg Lys Val Glu Val Tyr
            915                 920                 925

Ala Asp Ala Asp Glu Ile Leu Gln Glu Glu Ile Lys Glu Tyr Lys Ala
        930                 935                 940

Arg Leu Thr Cys Pro Cys Cys Asn Thr Arg Lys Lys Asp Ala Val Leu
945                 950                 955                 960

Thr Lys Cys Phe His Val Phe Cys Phe Glu Cys Val Arg Gly Arg Tyr
                965                 970                 975

Glu Ala Arg Gln Arg Lys Cys Pro Lys Cys Asn Ala Ala Phe Gly Ala
            980                 985                 990

His Asp Phe His Arg Ile Tyr Ile Ser
        995                 1000

<210> SEQ ID NO 54
<211> LENGTH: 789
<212> TYPE: PRT
<213> ORGANISM: Oryza sativa
<220> FEATURE:
<221> NAME/KEY: MISC_FEATURE
<223> OTHER INFORMATION: NP922769.1 in Fig. 10

<400> SEQUENCE: 54

Met Asp Ala Ala Ala Leu Gln Tyr Glu Asn Gln Lys Leu Val Gln Gln
1               5                   10                  15

Leu Glu Ala Gln Lys Ser Lys Met Arg Ala Leu Glu Gly Lys Phe Lys
            20                  25                  30

Glu Leu Arg Asp Glu Gln Cys Ser Tyr Asp Asn Thr Leu Ile Cys Leu
        35                  40                  45

Asn Lys Met Trp Asn Gln Leu Ile Asp Asp Leu Val Leu Leu Gly Val
    50                  55                  60

Arg Ala Gly Gly Asp Leu Asn Gly Leu Gln Ala Leu Asp His Glu Glu
65                  70                  75                  80

Met Ser Glu Glu Ser Leu Glu Ser Cys Pro Ser Glu Glu Ile Phe Leu
                85                  90                  95

Phe Arg Leu Leu Asn Ser Arg Asn Phe Arg Asn Asn Asp Asp Ser Ser
            100                 105                 110

Leu Ser Lys Leu Val Glu Glu Ala Leu Ala Leu Arg Tyr Ser Thr Thr
        115                 120                 125

Val Thr Leu Met Lys Ser Leu Gln Glu Ala Phe Ala Val Gln Gln Ala
    130                 135                 140

Arg Ser Glu Ser Leu Ser Leu Ala Leu Asn Gly Gln Asn Ser Ser Glu
```

-continued

```
            145                 150                 155                 160
        Asp Val Ile Val Ala Leu Glu Asn His Asn Asp Tyr Leu Lys Glu Val
                        165                 170                 175
        Val Asp Asn Leu Arg Gln Ala Val Ser Ile Ile Asn Arg Lys His Glu
                        180                 185                 190
        Lys Tyr Leu Asp Glu Ile Glu Ala Phe Lys Asn Asn Gln Ser Arg Glu
                        195                 200                 205
        Leu His Glu Val Lys Cys Leu Ser Gly Glu Leu Glu Glu Ser Met Ala
                        210                 215                 220
        Glu Leu Glu Glu Ser Arg Arg Lys Leu Ala Val Leu Gln Leu Gln Thr
        225                 230                 235                 240
        Gly Gly Gly Ser Leu Met Asn Thr Ser Ala Pro Asn Gly Val Asn Gly
                        245                 250                 255
        Ser Val Ser Thr Asp Lys Ser Ser Asp Lys Gly Met Gly Trp Arg Asp
                        260                 265                 270
        Leu Lys Asp Ala Val Glu Glu Ala Lys Thr Leu Ala Ala Asn Arg Leu
                        275                 280                 285
        Phe Glu Leu His Glu Thr Gln Glu Asp Asn Leu Ile Leu Ser Lys Gln
                        290                 295                 300
        Leu Glu Asp Ile Gln Asp Gln Leu Lys Asp Glu Asn Tyr Ile Val Thr
        305                 310                 315                 320
        Ser Lys Pro Tyr Thr Ile Leu Ser Asp Gln Leu His His Leu Asn Ala
                        325                 330                 335
        Glu Ile Glu Arg Tyr Arg Gly Leu Val Glu Val Leu Gln Ala Lys Ile
                        340                 345                 350
        Glu Asp Leu Glu His Glu Ile Gln Lys Leu Met Ala Glu Lys Asn Asp
                        355                 360                 365
        Leu Glu Ile Lys Ala Glu Ala Leu Gln Asp Ser Gly Lys Lys Asp
                        370                 375                 380
        Phe Lys Asp Glu Ile His Val Met Ala Ala Ser Leu Ser Lys Glu Met
        385                 390                 395                 400
        Glu Leu Leu Asp Asn Gln Met Asn Arg Ser Lys Asp Ala Ala Ser Glu
                        405                 410                 415
        Ala Leu Ala Leu Arg Glu Glu Ala Asp Tyr Leu Arg Thr Leu Leu Ala
                        420                 425                 430
        Lys Lys Ile Glu Thr Leu Asp Gln Glu Lys Gln Glu Leu Gln Phe Ile
                        435                 440                 445
        Val Asp Met Leu Gly Lys Glu Cys Ser Glu Ser Arg Ala Ile Ser Glu
                        450                 455                 460
        Ile Glu Glu Ser Glu Asn Arg Ala Arg Lys Gln Ala Glu Tyr Leu Arg
        465                 470                 475                 480
        Lys Cys Leu Glu Glu His Asn Leu Glu Leu Arg Val Lys Ala Ala Asn
                        485                 490                 495
        Glu Ala Glu Thr Ala Cys Gln Gln Arg Leu Ser Ile Ala Glu Ala Glu
                        500                 505                 510
        Leu Glu Asp Leu Arg Ala Lys Val Asp Ala Ser Glu Arg Asp Val Met
                        515                 520                 525
        Lys Leu Lys Glu Ser Ile Arg Ile Lys Glu Ala Glu Val Asp Gly His
                        530                 535                 540
        Ile Ser Glu Ile Glu Thr Ile Gly Gln Ala Tyr Glu Asp Met Gln Thr
        545                 550                 555                 560
        Gln Asn Gln His Leu Leu Gln Gln Val Ala Asp Arg Asp Asp Phe Asn
                        565                 570                 575
```

```
Ile Lys Leu Val Ser Asp Ser Val Lys Met Lys Gln Ala Tyr Gly Ser
            580                 585                 590

Leu Leu Ala Glu Lys Asn Met Leu Gln Lys Gln Leu Gln His Val Asn
            595                 600                 605

Ser Ser Leu Glu Ser Ser Lys Leu Lys Ile Thr Ser Gly Glu Glu Gln
            610                 615                 620

Met Lys Thr Tyr Val Ala Gln Ala Met Lys Ser Ser Ser Glu Asn Arg
625                 630                 635                 640

His Leu Ala Ile Ser Leu Glu Arg Thr Met Leu Glu Val Ser Asp Ala
                645                 650                 655

Glu Lys Glu Leu Lys Trp Leu Arg Ser Ala Thr Gly Ser Ala Glu Lys
            660                 665                 670

Glu Tyr Glu Ile Asn Gln Lys Lys Ile Ala Glu Leu Lys Met Glu Leu
            675                 680                 685

Glu Arg Glu Arg Asn Glu Arg Ile Lys Leu Glu Glu Tyr Glu Glu
            690                 695                 700

Val Lys Asn Glu Val Ser Glu Leu Thr Ser Glu Thr Glu Glu Thr Thr
705                 710                 715                 720

Ile Gln Lys Leu Gln Asp Glu Ile Lys Glu Cys Lys Ala Ile Leu Lys
                725                 730                 735

Cys Gly Val Cys Phe Asp Arg Pro Lys Glu Val Val Ile Thr Lys Cys
                740                 745                 750

Phe His Leu Phe Cys Ser Pro Cys Ile Gln Arg Asn Leu Glu Ile Arg
                755                 760                 765

His Arg Lys Cys Pro Gly Cys Gly Thr Pro Phe Gly Gln Ser Asp Val
        770                 775                 780

Arg Glu Val Lys Ile
785
```